US 7,462,472 B2

(12) United States Patent
Tang et al.

(10) Patent No.: US 7,462,472 B2
(45) Date of Patent: Dec. 9, 2008

(54) METHODS AND COMPOSITIONS RELATING TO ANTHRAX PATHOGENESIS

(75) Inventors: Wei-Jen Tang, Chicago, IL (US); Andrew Bohm, Stoneham, MA (US)

(73) Assignees: The University of Chicago, Chicago, IL (US); Boston Biomedical Research Institute, Watertown, MD (US)

( * ) Notice: Subject to any disclaimer, the term of this patent is extended or adjusted under 35 U.S.C. 154(b) by 472 days.

(21) Appl. No.: 10/286,452

(22) Filed: Nov. 1, 2002

(65) Prior Publication Data
US 2008/0124746 A1 May 29, 2008

Related U.S. Application Data

(60) Provisional application No. 60/336,762, filed on Nov. 2, 2001.

(51) Int. Cl.
*C12Q 9/00* (2006.01)
*C12Q 1/18* (2006.01)
(52) U.S. Cl. .................... 435/183; 435/32; 435/69.2; 424/130; 514/2
(58) Field of Classification Search .................. None
See application file for complete search history.

(56) References Cited

U.S. PATENT DOCUMENTS

| 4,652,521 | A | * | 3/1987 | Confer et al. ................. 435/34 |
| 5,183,745 | A | * | 2/1993 | Danchin et al. ............. 435/232 |
| 5,595,901 | A | * | 1/1997 | Rocancourt et al. ......... 435/232 |
| 5,698,518 | A | * | 12/1997 | Carson et al. ................. 514/12 |
| 6,107,076 | A | * | 8/2000 | Tang et al. .................. 435/232 |
| 6,197,928 | B1 | * | 3/2001 | Tsien et al. ................. 530/350 |
| 6,214,356 | B1 | * | 4/2001 | Guiso-Maclouf ........ 424/254.1 |
| 6,309,648 | B1 | * | 10/2001 | Betsou et al. ............. 424/203.1 |
| 6,333,154 | B1 | * | 12/2001 | Ladant et al. ................... 435/6 |
| 6,555,522 | B1 | * | 4/2003 | Iyengar et al. ................ 514/13 |
| 6,994,854 | B1 | * | 2/2006 | Betsou et al. ............ 424/150.1 |
| 2002/0045237 | A1 | * | 4/2002 | Karimova et al. ........... 435/199 |
| 2002/0106783 | A1 | * | 8/2002 | Ladant et al. ............ 435/252.1 |

(Continued)

FOREIGN PATENT DOCUMENTS

WO WO 84/03564 9/1984

OTHER PUBLICATIONS

Sarfati, Robert S et al, The Journal of Biological Chemistry, vol. 265(31) Nov. 5, pp. 18902-18906, 1990, Binding of 3'-Anthraniloyl-2'-deoxy-ATP to Calmodulin activated Adenylate Cyclase from *Bordetella pertussis* and *Bacillus anthracis*.*

(Continued)

*Primary Examiner*—Mark Navarro
*Assistant Examiner*—Ginny Allen Portner
(74) *Attorney, Agent, or Firm*—Fulbright & Jaworski LLP

(57) ABSTRACT

The structures of Edema Factor alone and Edema Factor bound to calmodulin without substrate has been crystallized and its structure determined by x-ray crystallography. Based upon these crystal structures, a method assaying for inhibitors of infection by a bacteria is presented which comprises obtaining a potential inhibitor, obtaining a calmodulin activated adenylyl cyclase exotoxin, obtaining calmodulin, admixing the potential inhibitor, the exotoxin, and the calmodulin, and assaying to determine whether or not the potential inhibitor inhibits production of cAMP by exotoxin.

7 Claims, 10 Drawing Sheets

U.S. PATENT DOCUMENTS

| | | | |
|---|---|---|---|
| 2002/0164632 A1* | 11/2002 | Kapeller-Libermann et al. | 435/6 |
| 2002/0188016 A9* | 12/2002 | Peterson et al. | 514/396 |
| 2003/0068650 A1* | 4/2003 | Greenblatt et al. | 435/7.1 |
| 2003/0082563 A1* | 5/2003 | Bell et al. | 435/6 |
| 2003/0157644 A1* | 8/2003 | Iyengar et al. | 435/69.1 |
| 2004/0029223 A1* | 2/2004 | Karimova et al. | 435/69.1 |
| 2004/0253245 A1* | 12/2004 | Briend et al. | 424/146.1 |
| 2005/0026866 A1* | 2/2005 | Pawelek | 514/54 |
| 2005/0148522 A1* | 7/2005 | Baasov et al. | 514/36 |
| 2005/0251345 A1* | 11/2005 | Bavari et al. | 702/19 |
| 2006/0166911 A1* | 7/2006 | Golz et al. | 514/44 |

OTHER PUBLICATIONS

Labruyere, E et al, Characterization of ATP and calmodulin-binding properties of a truncated form of Bacillus Anthracis adenylate cyclase, Biochemistry, vol. 29, pp. 4922-4928, 1990.*

Orlando, C et al, A monoclonal antibody directed against the catalytic site of Bacillus anthracis adenylyl cyclase identifies a novel mammalian brain catalytic subunit.*

Tippetts, M. Todd et al, Journal of Bacteriology, vol. 170(5), May 1988, pp. 2263-2266, Molecular cloning and expression of the Bacillus anthracis Edema Factor toxin gene: a calmodulin-dependent Adenylate Cyclase.*

Drum, Chester L et al, Nature, vol. 425, Jan. 24, 2002, pp. 396-402, Structural basis for the activation of the anthrax adenylyl cyclase exotoxin by calmodulin.*

Drum, Chester L et al, ACTA Cryst., 200, vol. D57, pp. 1881-1884, Crystallization and preliminary X-ray study of the edema factor exotoxin adenylyl cyclase domain from Bacillus anthracis in the presence of its activator, calmodulin.*

Kumar, P et al, Infection and Immunity, vol. 69(10), Oct. 2001, pp. 6532-6536, Purification of Anthrax Edema Factor from Eschericia coli and Identification of Residues Required for binding of Anthrax Protective Antigen.*

Munier, H et al, The Journal of Biological Chemistry, vol. 268(3), pp. 1695-1701, Jan. 25, 1993 Characterization of a Synthetic Calmodulin-binding peptide derived from Bacillus anthracis Adenylate Cyclase.*

Brown, SD et al, Infection and Immunity, 1977, vol. 18(1), pp. 85-93.*

Yahr, TL et al, PNAS (USA), vol. 95, pp. 13899-13904, Nov. 1998, ExoY, an adenylate cyclase by the Pseudomonas aeruginosa type III system.*

Brossier, Fabien et al, Infection and Immunity, vol. 68(4), pp. 1781-1786, Apr. 2000.*

Drum, Chester L et al, An Extended Conformation of Calmodulin Induceces Interactions between the structrual domains of Adenylyl cyclase from Bacillus anthracis to promote catalysis. The Journal of Biological Chemistry, vol. 275(46), p. 36334-36340, Nov. 17, 2000.*

Gentile, F et al, Eur. J. Biochem. vol. 175, pp. 447-453, 1988.*

Little, Stephen F. et al, Biochemical and Biophysical Research Communications, vol. 199(2), 1994, pp. 676-682, Mar. 15, 1994, Structure-Function analysis of Bacillus anthracis edema factor by using monoclonal antibodies.*

Patrizio, Mario et al, Journal of Neurochemistry, 2001, vol. 77, pp. 399-407, Human immunodeficiency virus type 1 tat protein decreases cyclic AMP synthesis in rat microglia cultures.*

Wang, Xiao-Quan et al, Biochemical and Biophysical Research Communications, vol. 228, pp. 81-87, 1996, Inhibition of Adenylyl cyclases by 12(S)-hydroxyeicosatetraenoic acid.*

Gallagher, D.T. et al, Journal of Molecular Biology, vol. 362(1), pp. 114-122, Sep. 2006, Structure of the Class IV Adenylyl Cyclase reveals a novel fold.*

Glaser, Phillippe et al, (1991) The EMBO Journal, vol. 10(7), pp. 1683-1688.*

Gentile, Fabrizio et al, Eur. J. Biochem, vol. 175, pp. 447-453, 1988.*

Sarfati, R.S et al, The Journal of Biological Chemistry, vol. 265(31), Nov. 5, 1990. pp. 18902-18906.*

Yahr, T.L. et al, PNAS, vol. 95, pp. 13899-13904, Nov. 1998, Microbiology.*

Babu et al., "Three-dimensional structure of calmodulin," Nature, 315:37-40, 1985.

Baillie and Read, "Bacillus anthracis, a bug with attitude," Curr. Opin. Microbiol., 4:78-81, 2001.

Bennett et al., "Kinetic characterization of the interaction of biotinylated human interleukin 5 with an Fc chimera of its receptor α subunit and development of an ELISA screening assay using real-time interaction biosensor analysis," J. Molec. Recog., 8:52-58, 1995.

Bieger and Essen, "Structural analysis of adenylate cyclases from Trypanosoma brucei in their nomomeric state," EMBO J., 20:443-445, 2001.

Bricogne, "Maximum-entropy methods and the Bayesian Programme," 1997 found at http://www.ccp4.ac.uk/courses/proceedings/1997/g_bricogne/main.html.

Brunger et al., "Crystallography and NMR system: A new software suite for macromolecular structure determination," Acta Crystallogr D., 54:905-921, 1998.

Chattopadhyaya et al., "Calmodulin structure refined at 1.7 Å resolution," J. Mol. Biol. 228:1177-1192, 1992.

Cowtan, "'dm': an automated procedure for phase improvement by density modification," Joint CCP4 and ESF-EAMCB Newsletter on Protein Crystallography, 31:34-38, 1994.

Deisseroth et al., "Translocation of calmodulin to the nucleus supports CREB phosphorylation in hippocampal neurons," Nature, 392:198-202, 1998.

DiAntonio, "Translating activity into plasticity," Nature, 405:1011-1012, 2000.

Dixon et al., "Antrhax", N. Engl. J. Med., 341:815-826, 1999.

Doman et al., "Molecular docking and high-throughput screening for novel inhibitors of protein tyrosine phosphatase-1B," J. Medicinal Chem., 45:2213-2221, 2002.

Drum et al., "An extended conformation of calmodulin induces interactions between the structural domains of adenylyl cyclase from Bacillus anthracis to promote catalysis," J. Biol. Chem., 275:36334-36340, 2000.

Drum et al., "Crystallization and preliminary X-ray study of the edema factor exotoxin adenylyl cyclase domain from Bacillus anthracis in the presence of its activator, calmodulin," Acta Crystallogr. D. Biol. Crystallogr, D57:1881-1884, 2001.

Dunlap (ed.), Immobilized Biochemicals and Affinity Chromatography, Adv. Exp. Med. Biol. 42, Plenum Press, N.F. 1974.

Ehlers and Augustine, "Calmodulin at the channel gate," Nature, 399:105-108, 1999.

Esnouf, Further additions to MolScript version 1.4, including reading and contouring of electron-density maps, Acta Crystallogr D. Biol. Crystallogr, D55:938-940, 1999.

Farrar et al., "Features of calmodulin that are important in the activation of the catalytic subunit of phosphorylase kinase," J. Biol. Chem., 268:4120-4125, 1993.

Finn et al., "Calcium-induced structural changes and domain autonomy in calmodulin," Nat. Struct. Biol., 2:777-783, 1995.

Galburt et al., "A novel endonuclease mechanism directly visualized for I-PpoI," Nat. Struct. Biol., 6:1096-1099, 1999.

Gibrat et al., "Surprising similarities in structure comparison," Curr. Opin. Struct. Biol., 6:377-385, 1996.

Glaser et al., Functional consequences of single amino acid substitutions in calmodulin-activated adenylate cyclase of Bordetella pertussis, EMBO J., 10:1683-1688, 1991.

Hayashi et al., "The binding of myristolylated N-terminal nonapeptie from neuro-specific protein CAP-23/NAP-22 to calmodulin does not induce the globular structure observed for the calmodulin-nonmyristylated peptide complex," Protein Sci., 9:1905-1913, 2000.

Huang et al., "Structure of a WW domain containing fragment of dystrophin in complex with beta-dystroglycan," Nat. Struct. Biol., 7:634-638, 2000.

Huber et al., "Multiple-sited interaction of caldesmon with $Ca^{2+}$-calmodulin," Biochem. J., 316:413-420, 1996.

Jakoby and Wilchek, "Affinity Techniques," In: Advances in Enzyme Regulation, Enzyme Purification, Part B, Meth. Enz. 34 Jakoby and Wilchek (Eds.), Acad. Press, N.Y., 1974.

Johanson et al., "Binding interactions of human interleukin 5 with its receptor α subunit," *J. Biol. Chem.*, 270(16):9459-9471, 1995.

Jones et al., "Improved methods for building protein models in electron density maps and the location of errors in these models," *Acta Cryst.*, A47:110-119, 1991.

Kabsch, "Automatic processing of rotation diffraction data from crystals of initially unknown symmetry and cell constants," *J. Appl. Cryst.*, 26:795-800, 1993.

Kleywegt and Jones, "Software for handling macromolecular envelopes," *Acta Crystallogr D. Biol. Crystallogr*, D55:941-944, 1999.

Kleywegt and Read, "Not your average density," *Structure*, 5:1557-1569, 1997.

Knight, "RSPS version 4.0: a semi-interactive vector-search program for solving heavy-atom derivatives," *Acta Crystallogr D. Biol. Crystallogr.*, D56:42-47, 2000.

Kraulis, "Molscript: a program to produce both detailed and schematic plots of protein structures," *J. Appl. Crystallogr*, 24:946-950, 1991.

Krueger et al., "Activation of myosin light chain kinase requires translocation of bound calmodulin," *J. Biol. Chem.*, 276:4535-4538, 2001.

Kuboniwa et al., "Solution structure of calcium-free calmodulin," *Nat. Struct. Biol.*, 2:768-776, 1995.

Labruyure et al., "Characterization of ATP and calmodulin-binding properties of a truncated form of *Bacillus anthracis* adenylate cyclase," *Biochemistry*, 29:4922-4928, 1990.

Ladant and Ullmann, "*Bordatella pertussis* adenylate cyclase: a toxin with multiple talents," *Trends Microbiol.*, 7:172-176, 1999.

LaFortelle and Bricogne, "Maximum-likelihood heavy-atom parameter refinement for multiple isomorphous replacement and multiwavelength anomalous diffraction methods," *Methods in Enzymology*, 276:472-494, 1997.

Leppla, "Anthrax toxin edema factor: a bacterial adenylate cyclase that increases cyclic AMP concentrations of eukaryotic cells," *Proc. Natl. Acad. Sci. USA*, 79:3162-3166, 1982.

Leppla, "Anthrax toxins," In: *Bacterial toxins and virulenece factors in disease*, Moss et al., (Eds.), NY, Base, Hong Kong Mercel Kekker, 543-572, 1995.

Leppla, "*Bacillus anthracis* calmodulin-dependent adenylate cyclase: chemical and enzymatic properties and interactions with eucaryotic cells," *Adv. Cyclic Nucleotide Protein Phosphorylation Res.*, 17:189-198, 1984.

Lewit-Bentley and Rety, "EF-hand calcium-binding proteins," *Curr. Opin. Struct. Biol.*, 10:637-643, 2000.

Lo Conte et al., "The atomic structure of protein-protein recognition sites," *J. Mol. Biol.*, 285:2177-2198, 1999.

Lorber et al., "Protein-protein docking with multiple residue conformations and residue substitutions," *Protein Science*, 11:1393-1408, 2002.

Masure et al., "Purification and assay of cell-invasive form of calmodulin-sensitive adenylyl cyclase from *Bordetella pertussis*," *Methods in Enzymol.*, 195:137-152, 1991.

Masure et al., The interaction of $Ca^{2+}$ with the calmodulin-sensitive adenylate cyclase from *Bordetella pertussis*, *J. Biol. Chem.*, 263:6933-6940, 1988.

Meador et al., "Target enzyme recognition by calmodulin: 2.4 A structure of a calmodulin-peptide complex," *Science*, 257:1251-1255, 1992.

Meador et al., "Modulation of calmodulin plasticity in molecular recognition on the basis of x-ray structures," *Science*, 262:1718-1721, 1993.

Meng et al., "Structure of the amino-terminal domain of Cbl complexed to its binding site on ZAP-70 kinase," *Nature*, 398:84-90, 1999.

Michankin et al., "Adenylate-cyclase," *Bulletin de la Societe de Pathologie Exotique*, 85:17-21, 1992, the an English summary.

Miller et al., "The active site of *Serratia* endonuclease contains a conserved magnesium-water cluster," *J. Mol. Biol.*, 288:975-987, 1999.

Mock and Fouet, "Anthrax", *Annul Rev. Microbiol.*, 55:647-671, 2001.

Montgomery et al., "Removal of a putative inhibitory element reduces the calcium-dependent calmodulin activation of neuronal nitric-oxide synthase," *J. Biol. Chem.*, 275:5052-5058, 2000.

Munier et al., "Structural characterization by nuclear magnetic resonance spectroscopy of a genetically engineered high-affinity calmodulin-binding peptide derived from *Bordetella pertussis* adenylate cyclase," *Arch. Biochem. Biphys.*, 320:224-235, 1995.

Munier et al., "The role of histidine 63 in the catalytic mechanism of *Bordetella pertussis* adenylate cyclase," *J. Biol. Chem.*, 267:9816-9820, 1992.

Nakamura et al., "Enzyme immunoassays: heterogeneous and homogeneous systems," In: *Handbook of Experimental Immunology* (4th Ed.), Weir, Herzenberg, Blackwell, Herzenberg, (eds). vol. 1, Chapter 27, Blackwell Scientific Publ., Oxford, 27.127.20, 1987.

Nassar et al., "Structures of Cdc42 bound to the active and catalytically compromised forms of Cdc42GAP," *Nat. Struct Biol.*, 5:1047-1052, 1998.

Nicholls et al., "Protein folding and association: insights from the interfacial and thermodynamic properties of hydrocarbons," *Proteins*, 11:281-296, 1991.

Osawa et al., "A novel target recognition revealed by -calmodulin in complex $Ca^{2+}$-calmodulin-dependent kinase kinase," *Nat. Struct. Biol.*, 6:819-824, 1999.

Otwinowski and Minor, "Processing of X-ray Diffraction Data Collected IN Oscillation Mode," Carter and Sweet (Eds.), In: *Methods in Enzymology*, Academic Press, 276: 307-327, 1997.

Parkhill et al., "Genome sequence of *Yersinia pestis*, the causative agent of plague," *Nature* 413:523-527, 2001.

Peters and Mayer, "$Ca^{2+}$/calmodulin signals the completion of coking and triggers a late step of vacuole fusion," *Nature*, 396:575-580, 1998.

Pitt et al., "Molecular basis of calmodulin tethering and $Ca^{2+}$-dependent inactivation of L-type $Ca^{2+}$ channels," *J. Biol. Chem.*, 276:30794-30802, 2001.

Powers and Shoichet, "Structure-based approach for binding site identification on AmpC β-lactamase," *J. Medicinal Chem.*, 45:3222-3234, 2002.

Read, "Improved Fourier coefficients for maps using phases from partial structures with errors," *Acta Cryst.*, A42:140-149, 1986.

Rhoads and Friedberg, "Sequence motifs for calmodulin recognition," *FASEB J.*, 11:331-340, 1997.

Rittinger et al., "Structure at 1.65 A of RhoA and its GTPase-activating protein in complex with a transition-state analogue," *Nature*, 389:758-762, 1997.

Scheffzek et al., "The Ras-RasGAP complex: structural basis for GTPase activation and its loss in oncogenic Ras mutants," *Science*, 277:333-338, 1997.

Scherer and Graff, "Calmodulin differentially modulates Smad1 and Smad2 signaling," *J. Biol. Chem.*, 275:41430-41438, 2000.

Schumacher et al., "Structure of gating domain of a $Ca^{2+}$-activated $K^+$ channel complexed with $Ca^{2+}$/calmodulin," *Nature*, 410:1120-1124, 2001.

Shevchenko and Mishankin, "Adenylyl cyclase of the causative agent of plague: its purification and properties," *Zh Mikrobiol. Epidemiol. Immunobiol.*, 7:59-63, 1987, article in Russian.

Shoichet et al., "Lead discovery using molecular docking," *Current Opin. Chem. Biol.*, 6:439-446, 2002.

Shoichet et al., "Ligand solvation in molecular docking," *Proteins: Structure, Function, and Genetics*, 34:4-16, 1999.

Stein et al., "The crystal structure of pertussis toxin," *Structure*, 2:45-57, 1994.

Su et al., "Docking molecules by families to increase the diversity of hits in database screen: computational strategy and experimental evaluation," *Proteins: Structure, Function, and Genetics*, 42:279-293, 2001.

Swanljung-Collins and Collins, "$Ca^{2+}$ stimulates the $Mg^{2+}$-ATPase activity of brush border myosin I with three or four calmodulin light chains but inhibits with less than two bound," *J. Biol. Chem.*, 266:1312-1319, 1991.

Tang and Hurley, "Catalytic mechanism and regulation of mammalian adenylyl cyclases," *Mol Pharmacol.*, 54:231-240, 1998.

Tang et al., "Expression and characterization of calmodulin-activated (typeI) adenylylcyclase," *J. Biol. Chem.*, 266:8595-8603, 1991.

Terwilliger and Berendzen, "Automated MAD and MIR structure solution," *Acta Crystallogr D. Biol. Crystallogr*, D55:849-861, 1999.

Tesmer et al., "Crystal structure of the catalytic domains of adenylyl cyclase in a complex with G$sa$GTPγS," *Science*, 278:1907-1916, 1997.

Tesmer et al., "Structure of RGS4 bound to AIF$_4$-activated G$ia_1$:stabilization of the transition state for GTP hydrolysis," *Cell*, 89:251-261, 1997.

Tesmer et al., "Two-metal-Ion catalysis in adenylyl cyclase," *Science*, 285:756-760, 1999.

Trewhella et al., "Small-angle scattering studies show distinct conformations of calmodulin in its complexes with two peptides based on the regulatory domain of the catalytic subunit of phosphorylase kinase," *Biochemistry*, 29:9316-9324, 1990.

VanEldik and Watterson, *Calmodulin and signal transduction*, 1998.

Wang et al., "Calmodulin binds to caldesmon in an antiparallel manner," *Biochemistry*, 36:15026-15034, 1997.

Weeks and Miller, "The design and implementation of SnB version 2.0," *J. Appl. Cryst.*, 32:120-124, 1999.

Wei et al., "A model binding site for testing scoring functions in molecular docking," *J. Mol. Biol.*, 322:339-355, 2002.

Wilson and Brunger, "The 1.0 Å crystal of $Ca^{2+}$-bound calmodulin: an analysis of disorder and implications for functionally relevant plasticity," *J. Mol. Biol.*, 301:1237-1256, 2000.

Yahr et al., "ExoY, an adenylate cyclase secreted by the *Pseudomonas aeruginosa* type III system," *Proc. Natl. Acad. Sci. USA*, 95:13899-13904, 1998.

Yan et al., "The conserved asparagine and arginine are essential for catalysis of mammalian adenylyl cyclase," *J. Biol Chem.*, 272:12342-12349, 1997.

Zhang et al., "Calcium-induced conformational transition revealed by the solution structure of apo calmodulin," *Natl. Struct. Biol.*, 2:758-767, 1995.

\* cited by examiner

SEQUENCE LISTING

<160> NUMBER OF SEQ ID NOS: 3

<210> SEQ ID NO 1
<211> LENGTH: 510
<212> TYPE: PRT
<213> ORGANISM: Bacillus anthracis

<400> SEQUENCE: 1

```
Asp Arg Ile Asp Val Leu Lys Gly Glu Lys Ala Leu Lys Ala Ser Gly
1               5                   10                  15

Leu Val Pro Glu His Ala Asp Ala Phe Lys Lys Ile Ala Arg Glu Leu
            20                  25                  30

Asn Thr Tyr Ile Leu Phe Arg Pro Val Asn Lys Leu Ala Thr Asn Leu
        35                  40                  45

Ile Lys Ser Gly Val Ala Thr Lys Gly Leu Asn Val His Gly Lys Ser
    50                  55                  60

Ser Asp Trp Gly Pro Val Ala Gly Tyr Ile Pro Phe Asp Gln Asp Leu
65                  70                  75                  80

Ser Lys Lys His Gly Gln Gln Leu Ala Val Glu Lys Gly Asn Leu Glu
                85                  90                  95

Asn Lys Lys Ser Ile Thr Glu His Glu Gly Glu Ile Gly Lys Ile Pro
            100                 105                 110

Leu Lys Leu Asp His Leu Arg Ile Glu Glu Leu Lys Glu Asn Gly Ile
        115                 120                 125

Ile Leu Lys Gly Lys Lys Glu Ile Asp Asn Gly Lys Lys Tyr Tyr Leu
    130                 135                 140

Leu Glu Ser Asn Asn Gln Val Tyr Glu Phe Arg Ile Ser Asp Glu Asn
145                 150                 155                 160

Asn Glu Val Gln Tyr Lys Thr Lys Glu Gly Lys Ile Thr Val Leu Gly
                165                 170                 175

Glu Lys Phe Asn Trp Arg Asn Ile Glu Val Met Ala Lys Asn Val Glu
            180                 185                 190

Gly Val Leu Lys Pro Leu Thr Ala Asp Tyr Asp Leu Phe Ala Leu Ala
        195                 200                 205

Pro Ser Leu Thr Glu Ile Lys Lys Gln Ile Pro Gln Lys Glu Trp Asp
    210                 215                 220

Lys Val Val Asn Thr Pro Asn Ser Leu Glu Lys Gln Lys Gly Val Thr
225                 230                 235                 240
```

```
Asn Leu Leu Ile Lys Tyr Gly Ile Glu Arg Lys Pro Asp Ser Thr Lys
            245                 250                 255

Gly Thr Leu Ser Asn Trp Gln Lys Gln Met Leu Asp Arg Leu Asn Glu
        260                 265                 270

Ala Val Lys Tyr Thr Gly Tyr Thr Gly Gly Asp Val Val Asn His Gly
    275                 280                 285

Thr Glu Gln Asp Asn Glu Glu Phe Pro Glu Lys Asp Asn Glu Ile Phe
290                 295                 300

Ile Ile Asn Pro Glu Gly Glu Phe Ile Leu Thr Lys Asn Trp Glu Met
305                 310                 315                 320

Thr Gly Arg Phe Ile Glu Lys Asn Ile Thr Gly Lys Asp Tyr Leu Tyr
            325                 330                 335

Tyr Phe Asn Arg Ser Tyr Asn Lys Ile Ala Pro Gly Asn Lys Ala Tyr
        340                 345                 350

Ile Glu Trp Thr Asp Pro Ile Thr Lys Ala Lys Ile Asn Thr Ile Pro
    355                 360                 365

Thr Ser Ala Glu Phe Ile Lys Asn Leu Ser Ser Ile Arg Arg Ser Ser
370                 375                 380

Asn Val Gly Val Tyr Lys Asp Ser Gly Asp Lys Asp Glu Phe Ala Lys
385                 390                 395                 400

Lys Glu Ser Val Lys Lys Ile Ala Gly Tyr Leu Ser Asp Tyr Tyr Asn
            405                 410                 415

Ser Ala Asn His Ile Phe Ser Gln Glu Lys Lys Arg Lys Ile Ser Ile
        420                 425                 430

Phe Arg Gly Ile Gln Ala Tyr Asn Glu Ile Glu Asn Val Leu Lys Ser
    435                 440                 445

Lys Gln Ile Ala Pro Glu Tyr Lys Asn Tyr Phe Gln Tyr Leu Lys Glu
450                 455                 460

Arg Ile Thr Asn Gln Val Gln Leu Leu Leu Thr His Gln Lys Ser Asn
465                 470                 475                 480

Ile Glu Phe Lys Leu Leu Tyr Lys Gln Leu Asn Phe Thr Glu Asn Glu
            485                 490                 495

Thr Asp Asn Phe Glu Val Phe Gln Lys Ile Ile Asp Glu Lys
        500                 505                 510

<210> SEQ ID NO 2
<211> LENGTH: 532
<212> TYPE: PRT
<213> ORGANISM: Bordetella pertussis

<400> SEQUENCE: 2

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
            85                  90                  95

Asp Asn Asp Val Asn Ser Ser Leu Ala His Gly His Thr Ala Val Asp
        100                 105                 110
```

-continued

```
Leu Thr Leu Ser Lys Glu Arg Leu Asp Tyr Leu Arg Gln Ala Gly Leu
        115                 120                 125

Val Thr Gly Met Ala Asp Gly Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Ile Asp Met Phe
                180                 185                 190

Ala Ile Met Pro His Leu Ser Asn Phe Arg Asp Ser Ala Arg Ser Ser
            195                 200                 205

Val Thr Ser Gly Asp Ser Val Thr Asp Tyr Leu Ala Arg Thr Arg Arg
        210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Phe Arg Gly Ser Ser Arg Trp
        515                 520                 525
```

```
-continued

Ala Gly Gly Phe
    530

<210> SEQ ID NO 3
<211> LENGTH: 148
<212> TYPE: PRT
<213> ORGANISM: Homo sapiens

<400> SEQUENCE: 3

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145
```

METHODS AND COMPOSITIONS RELATING TO ANTHRAX PATHOGENESIS

This application claims priority to, and specifically incorporates herein by reference, U.S. Provisional Application Ser. No. 60/336,762 filed Nov. 2, 2001.

This invention was made with government support under grant number GM53459, GM62458, and DA05778 awarded by the National Institutes of Health. The government has certain rights in the invention.

FIELD OF THE INVENTION

The present invention generally relates to crystalline Edema Factor (EF) without substrate, crystalline Edema Factor-calmodulin complex without substrate and the structures of Edema Factor without substrate and Edema Factor-calmodulin complex as determined by x-ray crystallography. Specifically, this invention relates to the use of the structures of Edema Factor without substrate, Edema Factor-calmodulin complex, and any of its homologues, mutants and/or co-complexes of such structures to design modulators of calmodulin activation of Edema Factor.

BACKGROUND OF THE INVENTION

Many infectious organisms increase the internal cyclic AMP (cAMP) levels of infected host cells. Whereas, some do this through chemical modification of heterotrimeric G-proteins, at least four bacteria, *Bordetella pertussis* (Whooping cough), *Pseudomonas aeruginosa* (various nosocomial infections), *Yersinia pestis* (plague) and *Bacillus anthracis* (Anthrax) accomplish this by producing toxins with adenylyl cyclase activity (Leppla, 1982; Ladant and Ullmann, 1999; Yahr et al., 1998; Shevchenko and Mishankin, 1987; Parkhill et al., 2001; Michankin et al., 1992).

*Bacillus anthracis*, the bacterium responsible for anthrax is estimated to be responsible for 20,000-100,000 cases of naturally contracted anthrax per year, worldwide. Anthrax may cause death within 24 hours, preceded only by nondescript, flu-like symptoms (Hanna 1998). In part, because the spore form of the bacterium is easily stored for long periods, anthrax has undergone significant development as a biological weapon.

*Bacillus anthracis* defeats the host defense system by secreting three exotoxins, protective antigen, lethal factor and Edema Factor (EF) (Baillie and Read, 2001; Dixon et al., 1999; Mock and Fouet, 2001). Protective antigen, a pH-dependent transporter, binds and transports both lethal factor and Edema Factor into the cytosol of eukaryotic cells. Lethal factor, a zinc metalloprotease, cleave and inactivate mitogen-activated protein kinase kinase and possibly other cellular proteins in the macrophage (Duesbery et al., 1998). This results in the release of tumor necrosis factor a and interleukin-1 b which are partly responsible for sudden death in systemic anthrax. Edema Factor, a calmodulin (CaM)-activated adenylyl cyclase, can increase the level of intracellular cyclic AMP to a pathologic level, upsetting water homeostasis (Baillie and Read, 2001; Dixon et al., 1999; Mock and Fouet, 2001). EF is responsible for the massive Edema seen in cutaneous anthrax and impaired neutrophil function in systematic infection.

Edema Factor is a 92.5 kDa protein that can be roughly divided into two distinct domains (Leppla, 1998). The N-terminal 250 amino-acid region of EF is centrally involved in EF's association with protective antigen and entrance into host cells (Labruyere et al., 1990, Drum et al. 2000). The C-terminal, 510 amino acid region (amino acids 291-800) has calmodulin activated adenylyl cyclase activity (Labruyere et al., 1990, Drum et al. 2000). After gaining access to the cytoplasm, Edema Factor binds calmodulin at the resting calcium concentration and is thus, activated to produce unregulated levels of cAMP within the cytosol of the host cell (Leppla, 1984; Leppla, 1982). The rate of ATP conversion to cAMP by Edema Factor is two to three orders of magnitude greater than membrane-bound eukaryotic adenylyl cyclases (Labruyure et al, 1990; Tang et al., 1991).

Calmodulin is a 16.5 kDa prototypic calcium sensor involved in modulation of many intracellular processes including synaptic plasticity, control of gene transcription, ion conductivities, vesicular fusion, and learning (Deisseroth et al., 1998; DiAntonio, 2000; Ehlers and Augustine, 1999; Peters and Mayer, 1998). Calmodulin transduces intracellular calcium signals via two globular domains connected by a flexible, central a-helix. Each globular domain is composed of two helix-loop-helix "EF-hand" calcium binding motifs (Babu et al., 1985; Chattopadhyaya et al., 1992; Wilson and Brunger, 2000). Calcium binding shifts these domains from a mainly hydrophilic, closed state, to an open conformation exposing a large, hydrophobic binding pocket (Kuboniwa et al., 1995; Finn et al., 1995). An exceptionally broad array of effector molecules are regulated through interaction with CaM, including enzymes that control diffuisible messengers and that alter the state of protein phosphorylation, molecules that modulate ion conductivity, and cytoskeletal proteins (Eldik and Watterson, 1998). Although the structure of CaM has been solved in complex with an assortment of effector fragments, none of these complexes has contained active enzymes or peptide fragments larger than 10 kDa.

The structural characterization of the adenylyl cyclase domain of EF holds promise for insight in several different areas. First, secreted adenylyl cyclases compose a multigene family of exotoxins produced by at least four distinct pathogenic bacteria, *Bacillus anthracis, Bordetella pertussis, Pseudomonas aeruginosa* and *Yersinia pestis*. The structural features peculiar to this homologous family may provide insight into overall functional themes of toxin activation and inhibition. Second, the catalytic rate of EF is approximately one hundred times faster than that of membrane bound adenylyl cyclases whose catalytic core domain has been structurally determined (Tesmer et al., 1997). With no sequence homology detectable between the two adenylyl cyclase families, a structural understanding of the active site of EF may yield a novel fold used for the cyclization of ATP or a variant on the di-metal mediated catalysis used by membrane-bound adenylyl cyclases (Tesmer et al., 1999). Third, the mechanism of activation with which the binding of calmodulin regulates the production of cyclic AMP in some pathogenic bacteria may hold implications for inhibitory strategies of the toxin as well as structural themes applicable to other calmodulin binding enzymes.

The inventors recently reported biochemical characterization of EF/CaM interaction (Drum et al., 2000). Drum et al. provided a detailed look of the interaction between CaM and EF, and suggested a catalytic mechanism for converting ATP to cAMP that is different from that seen in previously solved adenylyl cyclases (Tesmer et al., 1999). To understand the molecular detail in the catalytic site of EF and the interaction of EF with CaM, the inventors have solved two structures; the structure of EF without CaM or substrate, and the structure of EF with CaM, but without substrate. Comparison of these structures, along with mutational analysis reveals that the key step in CaM activation of EF is the removal of an inhibitory domain which is distant from the active site and the stabilization of a catalytic loop. Such understanding of this mechanism not only gives a first molecular insight into how CaM activates EF, but also provides potential avenues for modulating CaM activation of EF.

The present invention discloses these structures and also discloses various methods of screening assays to identify small molecules that modulate activation of EF by CaM and EF alone.

Adenylyl cyclase toxins are known to be secreted by two other human pathogens, *Bordetella pertussis* (CyaA) and *Pseudomonas aeruginosa* (ExoY) which cause whooping cough and 10-20% of hospital-acquired infections, respectively (Ladant and Ullmann, 1999; Yahr et al, 1998). Immunocompromised patients, such as, cystic fibrosis and AIDS patients, are particularly vulnerable. Since these pathogens can be hospital acquired, they are likely to harbor many antibiotic resistance. Thus, many antibiotics can be ineffective in fighting against such infections. Accordingly, better drugs against these pathogens will likely be useful to block the toxic effects caused by the infection of these pathogens.

Also, biochemical studies have shown that *Yersinia pestis*, the bacterium that causes plague, also secretes an adenylyl cyclase toxin and genome sequence identified a gene in *Yersinia pestis* for such a toxin (Shevchenko and Mishankin, 1987; Parkhill et al., 2001; Michankin et al., 1992). *Yersinia pestis* is primarily a rodent pathogen which is usually transmitted subcutaneously to humans by the bite of an infected flea.

The structure of Edema Factor discovered by the inventors can be useful in discovering small molecules that can be useful against the infection of *Bacillus anthracis*, *Bordetella pertussis*, *Pseudomonas aeruginosa* and *Yersinia pestis*.

SUMMARY OF THE INVENTION

The present invention overcomes the deficiencies in the art by providing methods of assaying for an inhibitor of infection by a bacteria by obtaining a potential inhibitor, a calmodulin activated adenylyl cyclase exotoxin, calmodulin and admixing the potential inhibitor, the exotoxin and the calmodulin and then assaying to determine whether or not the potential inhibitor inhibits production of cAMP by the exotoxin. As used herein, the terms "inhibitor," "inhibit," and "inhibition" are defined as a complete inactivation or reduced activation of exotoxin activity. The present invention also provides for methods of assaying for an inhibitor of the bacterial infections *Bacillus anthracis*, *Bordetella purtussis*, *Pseudomonas aeruginosa* and/or *Yersinia pestis*. In certain embodiments, the exotoxin is Edema factor and its sequence homologs from *Bacillus anthracis*, *Bordetella purtussis*, *Pseudomonas aeruginosa* and/or *Yersinia pestis*. The present invention also contemplates obtaining the potential inhibitor comprising selecting the potential inhibitor by structural based inhibitor discovery. In other embodiments, the calmodulin activated adenylyl cyclase exotoxin is Edema Factor from *Bacillus anthracis*. In yet another embodiment, the calmodulin activated adenylyl cyclase exotoxin is a homolog of *Bacillus anthracis* Edema Factor from *Pseudomonas aeruginosa* or *Yersinia pestis*.

In other embodiments, the potential inhibitor is a protein, a small molecule, a modified nucleotide, or an antibody. The potential inhibitor is obtained by designing the potential inhibitor to form non-covalent bonds with amino acids of Edema Factor, calmodulin, Edema Factor/calmodulin complex with substrate, and/or Edema Factor/calmodulin complex without substrate, based upon the crystal structure of Edema Factor, calmodulin, Edema Factor/calmodulin complex with substrate, and/or Edema Factor/calmodulin complex without substrate. In certain embodiments, the potential inhibitor is designed to bind the adenylyl cyclase domain of Edema Factor, the active site of the adenylyl cyclase domain of Edema Factor, the calmodulin binding domain of Edema Factor, or the Edema Factor binding domain of calmodulin. In another embodiment, the potential inhibitor is designed to bind the amino acid $Arg^{329}$, $Lys^{346}$, $Lys^{353}$, $Asp^{491}$ and/or $Asp^{493}$, $His^{577}$, $His^{351}$, $Lys^{525}$, $Lys^{372}$, $Thr^{548}$, $Thr^{579}$ $As^{583}$ $Glu^{588}$, $Asp^{590}$, $Asp^{647}$, $Asn^{639}$, and/or $Pro^{587}$.

In other embodiments, the potential inhibitor is designed to bind at least 1, 2, 5, 10, 20, 30, 40, 50, 60, 75, 100, 150, 200 and/or 508 or more contiguous amino acids including any integer derivable therein, and any range derivable therein, of the adenylyl cyclase domain of Edema Factor, which is found at approximately amino acids 291-800 of Edema Factor. As used herein, "any integer derivable therein" means a integer between the numbers described in the specification, and "any range derivable therein" means any range selected from such numbers or integers. In other embodiments, the potential inhibitor will bind the adenylyl cyclase domain of Edema Factor, which is found at approximately amino acids 291-800 of Edema Factor.

In one embodiment, the potential inhibitor is designed to bind at least 2, 5, 10, 15, 20, 40 and/or 57 or more contiguous amino acids including any integer derivable therein, and any range derivable therein, of the $C_A$ domain of Edema Factor, which is found at approximately amino acids 291-349 of Edema Factor. In another embodiment, the potential inhibitor is designed to bind the $C_A$ domain of Edema Factor, which is found at approximately amino acids 291-349 of Edema Factor.

In still another embodiment, the potential inhibitor is designed to bind at least 2, 5, 10, 15, 20, and/or 41 or more contiguous amino acids including any integer derivable therein, and any range derivable therein, of the $C_A$ domain of Edema Factor, which is found at approximately amino acids 490-622 of Edema Factor. In another embodiment, the potential inhibitor is designed to bind the $C_A$ domain of Edema Factor, which is found at approximately amino acids 490-622 of Edema Factor.

In another embodiment, the potential inhibitor is designed to bind at least 2, 5, 10, 15, 20, 40, 50, 100 and/or 138 or more contiguous amino acids including any integer derivable therein, and any range derivable therein, of the $C_B$ domain of Edema Factor, which is found at approximately amino acids 350-489 of Edema Factor. In another embodiment, the potential inhibitor is designed to bind the $C_B$ domain of Edema Factor, which is found at approximately amino acids 350-489 of Edema Factor.

In another embodiment, the potential inhibitor is designed to bind at least 2, 5, 10, 15, 20, 30, 40, 50, 75, 100 and/or 139 or more contiguous amino acids including any integer derivable therein, and any range derivable therein, of the helical domain of Edema Factor, which is found at approximately amino acids 660-800 of Edema Factor. In still another embodiment, the potential inhibitor is designed to bind the helical domain of Edema Factor, which is found at approximately amino acids 660-800 of Edema Factor.

In still another embodiment, the potential inhibitor is designed to bind at least 2, 5, 10, 15, 20 and/or 35 or more contiguous amino acids including any integer derivable therein, and any range derivable therein, of an extended linker that connects the helical domain to the $C_A$ of Edema Factor, which is found at approximately amino acids 623-659 of Edema Factor. In another embodiment, the potential inhibitor is designed to bind the extended linker that connects the helical domain to the $C_A$ of Edema Factor, which is found at approximately amino acids 623-659 of Edema Factor.

In yet another embodiment, the potential inhibitor is designed to bind at least 2, 5, 10, 15, 20 and/or 48 or more contiguous amino acids including any integer derivable therein, and any range derivable therein, of Switch A, which is found at approximately amino acids 502-551 of Edema Factor. In another embodiment, the potential inhibitor is designed to bind Switch A, which is found at approximately amino acids 502-551 of Edema Factor.

In still another embodiment, the potential inhibitor is designed to bind at least 2, 5, 10 and/or 12 or more contiguous amino acids including any integer derivable therein, and any range derivable therein, of Switch B, which is found at approximately amino acids 578-591 of Edema Factor. In another embodiment, the potential inhibitor is designed to bind Switch B, which is found at approximately amino acids 578-591 of Edema Factor.

In another embodiment, the potential inhibitor is designed to bind at least 2, 5, 10, 15, 20 and/or 28 or more contiguous amino acids including any integer derivable therein, and any range derivable therein, of Switch C, which is found at approximately amino acids 630-659 of Edema Factor. In still another embodiment, the potential inhibitor is designed to bind Switch C, which is found at approximately amino acids 630-659 of Edema Factor.

In yet another embodiment, the potential inhibitor is designed to bind at least 2, 5, 10, 15, 20 and/or 34 or more contiguous amino acids including any integer derivable therein, and any range derivable therein, of a domain of Edema Factor that binds calmodulin, which is found at approximately amino acids 501-536 of Edema Factor. In another embodiment, the potential inhibitor is designed to bind a domain of Edema Factor that binds calmodulin, which is found at approximately amino acids 501-536 of Edema Factor.

In still another embodiment, the potential inhibitor is designed to bind at least 2, 5, 10 and/or 13 or more contiguous amino acids including any integer derivable therein, and any range derivable therein, of a domain of Edema Factor that binds calmodulin, which is found at approximately amino acids 620-634 of Edema Factor. In one embodiment, the potential inhibitor is designed to bind a domain of Edema Factor that binds calmodulin, which is found at approximately amino acids 620-634 of Edema Factor.

In another embodiment, the potential inhibitor is designed to bind at least 2, 5, 10, 15, 20 and/or 24 or more contiguous amino acids including any integer derivable therein, and any range derivable therein, of a domain of Edema Factor that binds calmodulin, which is found at approximately amino acids 647-672 of Edema Factor. In one embodiment, the potential inhibitor is designed to bind a domain of Edema Factor that binds calmodulin, which is found at approximately amino acids 647-672 of Edema Factor.

In yet another embodiment, the potential inhibitor is designed to bind at least 2, 5, 10, 15 and/or 16 or more contiguous amino acids including any integer derivable therein, and any range derivable therein, of a domain of Edema Factor that binds calmodulin, which is found at approximately amino acids 690-707 of Edema Factor. In one embodiment, the potential inhibitor is designed to bind a domain of Edema Factor that binds calmodulin, which is found at approximately amino acids 690-707 of Edema Factor.

In another embodiment, the potential inhibitor is designed to bind the adenylyl cyclase domain of Edema Factor when Edema Factor is bound to calmodulin. In still another embodiment, the potential inhibitor is designed to bind the adenylyl cyclase domain of Edema Factor when Edema Factor is not bound to calmodulin. In another embodiment, the potential inhibitor is designed to bind the active site of the adenylyl cyclase domain of Edema Factor. In a further embodimentm the potential inhibitor is designed to bind the active site of the adenylyl cyclase domain of Edema Factor when Edema Factor is bound to calmodulin. In still a further embodiment, the potential inhibitor is designed to bind the calmodulin binding domain of Edema Factor. In yet another embodiment, the potential inhibitor is designed to bind the calmodulin binding domain of Edema Factor when Edema Factor is not bound to calmodulin. In still another embodiment, the potential inhibitor is designed to bind the calmodulin binding domain of Edema Factor when Edema Factor is bound to calmodulin. In another embodiment, the potential inhibitor is designed to bind the Edema Factor binding domain of calmodulin. In still another embodiment, the potential inhibitor is designed to bind the Edema Factor binding domain of calmodulin when Edema Factor is not bound to calmodulin. In another embodiment, the potential inhibitor is designed to bind the Edema Factor binding domain of calmodulin when Edema Factor is bound to calmodulin.

In another aspect of this invention, there is a process of identifying an inhibitor of a bacterial infection by obtaining a potential inhibitor, a calmodulin activated adenylyl cyclase exotoxin, and calmodulin and admixing the potential inhibitor, the exotoxin and the calmodulin and then assaying to determine whether or not the potential inhibitor inhibits production of cAMP by the exotoxin.

In yet another embodiment of present invention, there is a pharmaceutical composition comprising an inhibitor of a bacterial infection identified by a process comprising obtaining a potential inhibitor, a calmodulin activated adenylyl cyclase exotoxin and calmodulin and admixing the potential inhibitor, the exotoxin, and the calmodulin and then assaying to determine whether or not the potential inhibitor inhibits production of cAMP by the exotoxin.

In still another embodiment of the present invention, there is a method of inhibiting pathogenesis of a bacterial infection comprising; obtaining a pharmaceutical composition comprising an inhibitor of a bacterial infection identified by a process comprising obtaining a potential inhibitor, a calmodulin activated adenylyl cyclase exotoxin, and calmodulin, and then admixing the potential inhibitor, the exotoxin, and the calmodulin and assaying to determine whether or not the potential inhibitor inhibits production of cAMP by the exotoxin and then administering an effective amount of the pharmaceutical composition to a subject.

In yet another embodiment, there is a method of assaying for an inhibitor of infection by a bacteria comprising obtaining a potential inhibitor, obtaining an adenylyl cyclase exotoxin, admixing the potential inhibitor and the exotoxin and assaying to determine whether or not the potential inhibitor inhibits production of cAMP by the exotoxin. The bacterial infection can be *Pseudomonas aeruginosa* or *Yersinia pestis*. In other embodiments, the activated adenylyl cyclase exotoxin is an Edema Factor homolog. The Edema Factor homolog can be from *Pseudomonas aeruginosa* (ExoY) or *Yersinia pestis*. The adenylyl cyclase exotoxin can also be a homolog of *Bacillus Anthracis* Edema Factor from *Pseudomonas aeruginosa* or *Yersinia pestis*. The present invention also contemplates obtaining the potential inhibitor comprising selecting the potential inhibitor by structural based inhibitor discovery.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4A Ball-and-stick representations for the active site of EF alone catalytic site. FIG. 4B EF-CaM complex without nucleotide, and FIG. 4C EF-CaM complex with 3'dATP. $SO_4$ and 3'dATP in EF alone and EF-CaM-3'dATP complex, respectively are colored black and yellow, respectively. Metal ions are colored gray. Residues from switch A (540-551), switch B (578-592), switch C (634-642) and $C_A/C_B$ outside of the switch regions are shown in cyan, orange, magenta, and green, respectively.

FIG. 5A Ball-and-stick representation of the EF active site. Secondary structure elements and amino acid residues are colored green and blue, respectively. 3'd-ATP and metal are colored black and gray, respectively. FIG. 5B Proposed mechanism of catalysis of EF. For the clarity, only residues that are directly involved in 3' O$^-$ to α-phosphate nucleophilic attack are shown. FIG. 5C Ball-and-stick representation of the mAC active site. Secondary structure elements of C1a and C2a are colored green and yellow, respectively. Amino acid residues, ATPαS, and metals are colored blue, black, and gray, respectively. The O4', C4', and α-P of ATPαS is oriented similar to those of 3'd-ATP in FIG. 5A for comparison. FIG. 5D Secondary structures of the EF catalytic core and the mAC catalytic core. C1a and C2a of mAC are colored green and yellow, respectively. The view of EF and mAC is the same as in FIG. 5A and 5C, respectively.

FIG. 6A Ribbon representation of CaM and EF. CaM is colored red. Switch A, switch C, the helical domain and $C_A/C_B$ outside of the switch regions are shown in cyan, magenta, yellow, and green, respectively. FIG B Mutational analysis of EF residues that contact CaM. The adenylyl cyclase assay was performed with EF (5 ng), K525A (5 ng), and D647A (50 ng) at 30° C. for 10 min in the present of 5 mM ATP, 10 mM $MgCl_2$ and 0.05 mM $CaCl_2$.

FIG. 7A Ribbon representations of CaM alone, FIG. 7B CaM in complex with effector derived peptides from myosin light chain kinase, FIG. 7C the calcium sensitive potassium ion channel, and FIG. 7D Edema Factor. The C-terminal domain (red) of CaM is aligned based on helix VI of CaM. The CaM central helix and N-terminal domains are colored orange, and the effector peptides are colored blue. In FIG. 7E, the sequence and secondary structure of CaM is shown, with calcium-binding sites indicated, and calcium-binding residues colored red. The boxes beneath the CaM sequence indicate the effector contact area of each residue in the various structures, using the same coloring scheme as in FIG. 2. The PDB codes for the structures used in making this figure are 1CLL, 1CDL, 1CKK, 1CDM, and 1G4Y for CaM alone, and complexes with myosin light chain kinase, CaM dependent protein kinase, CaM dependent protein kinase II, and the gating domain of the small conductance potassium channel, respectively. The helix designations above the CaM sequence are based on the 1CLL CaM structure.

DETAILED DESCRIPTION OF THE INVENTION

I. The Present Invention

Figure 1:
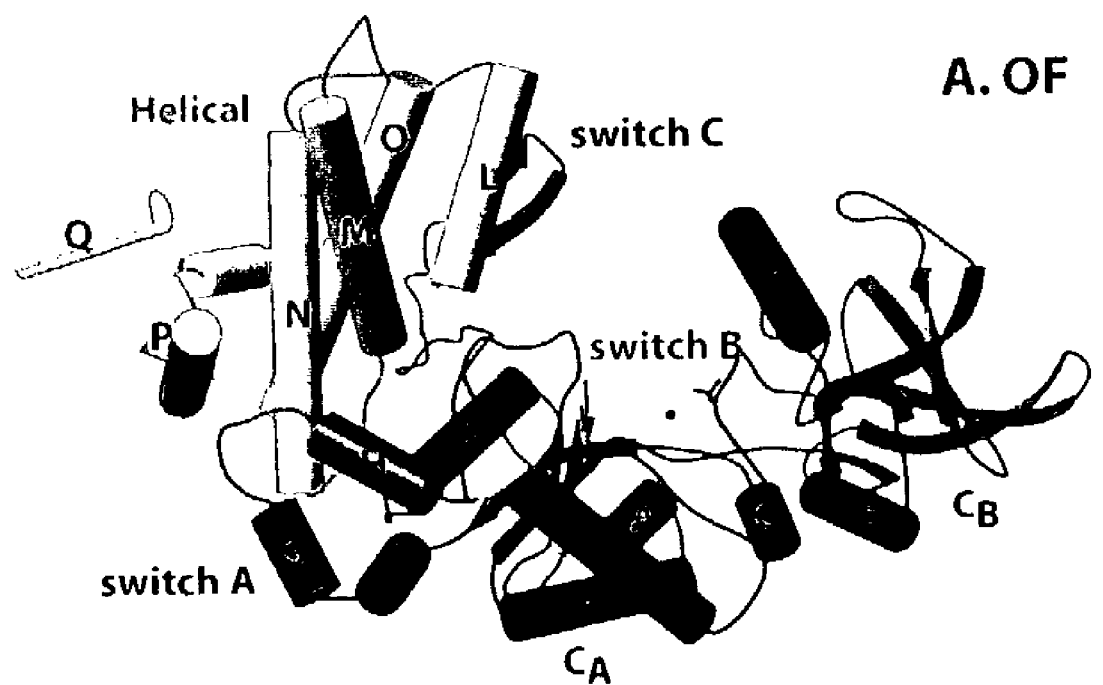
FIG. 1A and FIG. 1B Secondary structure representation of EF alone FIG. 1A and EF-CaM-3'dATP complex FIG. 1B. CaM (red) is held on one side by a fingerlike projection of CA, and on the other by switch C (magenta), and by the helical domain (yellow). Switch A and switch B is colored cyan and orange, respectively. The ATP analog and metal (purple) are bound between the two domains CA and CB (both colored green) which form the active site. In EF alone structure, the last two helices, P and Q (a.a. 771-799, white), which are not part of the CaM interface or the active site, are swapped between two EF molecules in the EF alone structure. This swap is unlikely to be physiological relevant since EF is a monomer based on gel exclusion column.
Figure 1:
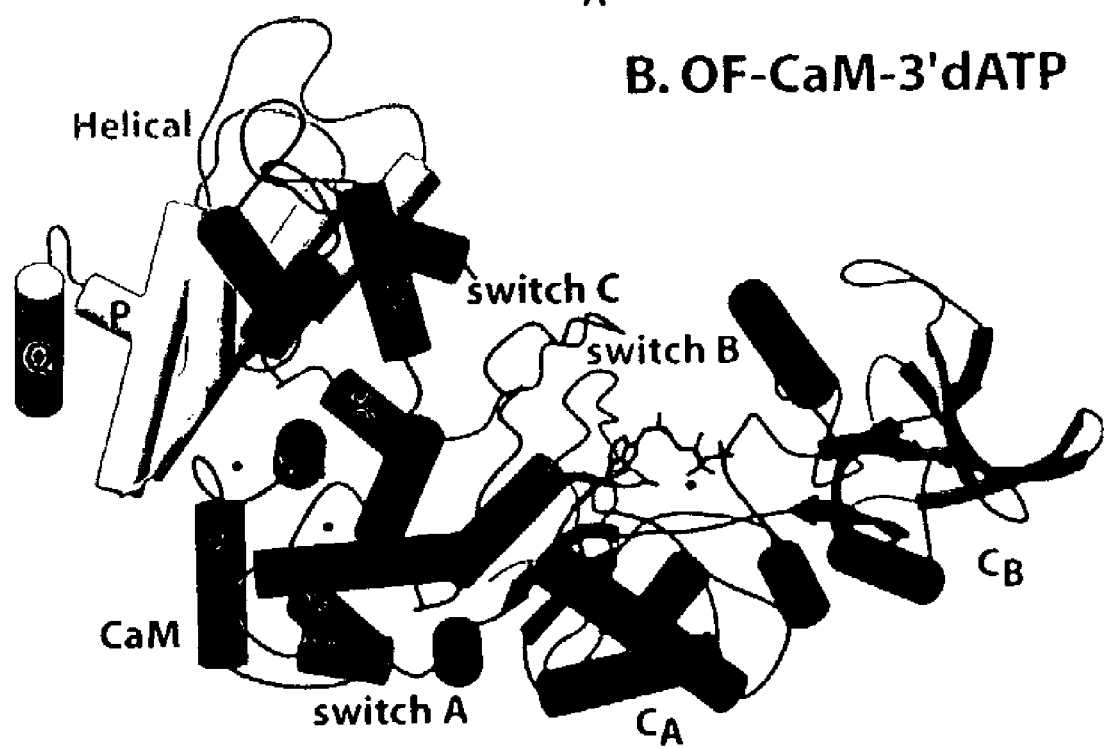

There have been suggestions and hypothetical models created to explain the mechanism by which calmodulin (CaM) interacts with and activates Edema Factor. While these suggestions have some accuracy, they have not proven beneficial for the development of small molecules that can be used to fight infection of *Bacillus anthracis,* the microbe that is the cause of anthrax. Thus, the need remains for a more detailed description of the mechanism by which CaM activates EF.

The structures of EF alone, without substrate, or of EF-CaM complex without substrate has not been discovered to date. Such structures are benficial for the discovery of small molecules that inhibits the activation of EF by CaM. Thus, the need remains for detailed descriptions of the EF structure without substrate and the EF-CaM complex without substrate.

The inventors have overcome the deficiencies in the prior art by elucidating the molecular structures of (1) EF without CaM or substrate and (2) the structure of EF with CaM. X-ray crystallography images of both structures have been determined and are disclosed by the inventors. A detailed description of the mechanism by which CaM activates EF is disclosed. Also, methods of using diagnostic assays to discover small molecules that can modulate EF activation by CaM are also disclosed.

The ability to inhibit the infection of a bacteria that secretes an adenylyl cyclase exotoxin is significant in that a number of bacterial infections are associated with an increase in cAMP levels in the host by secreting an adenylyl cyclase exotoxin, including; *Bacillus anthracis, Bordetella pertussis, Pseudomonas aeruginosa,* and/or *Yersinia pestis.* Any one of these bacterial infections could potentially be treated by inhibiting the activation of the secreted adenylyl cyclase exotoxin.

The findings of the inventors permit the development of novel assay methods for the identification of inhibitors of the activation of secreted adenylyl cyclase exotoxins.

II. Screening Assays

One important aspect of the invention concerns assays for screening for potential new inhibitors of the activation of secreted adenylylcyclase exotoxins. The assays may be carried out at the protein or nucleic acid level. Such assays may find use in diagnostic applications for directing the treatment of a patient infected with *Bacillus anthracis, Bordetella pertussis, Pseudomonas aeruginosa,* and/or *Yersinia pestis* and similarly, the assays may provide insight as to the relative efficacy of a given inhibitor of the activation of a secreted adenylyl cyclase exotoxin.

The invention provides methods for screening for novel inhibitors of the activation of adenylyl cyclase exotoxins. Such an inhibitor could affect the chemical modification of a molecule in the activation of adenylyl cyclase exotoxins, such as the inhibition of ATP from binding the catalytic site of the adenylyl cyclase exotoxin. In screening assays for polypeptide activity, the candidate substance may first be screened for basic biochemical activity—e.g., binding to a target molecule and then tested for its ability to regulate expression, at the cellular, tissue or whole animal level.

1. Drug Discovery by Structural Based Inhibitor Discovery

Molecular docking can be used to screen compound databases for novel ligands that complement the structure of a binding site (Shoichet et al., 1999; Lorber et al., 2002; Su et al., 2001; Shoichet et al., 2002). The chemical libraries with the known structures can be the compounds from the commercial available sources (i.e. Sigma-Aldrich, MayBridge) or those built by different chemists in the academic institutes or in the biotech or pharmaceutical companies. For example, Molecular Docking has been used to discover novel ligands of lysozyme, inhibitors of β-lactamase and Protein Tyrosine Phosphatase 1B (Powers and Shoichet, 2002; Doman et al., 2002; Wei et al., 2002). Based on the catalytic site of the EF/CaM model, one can define a set of spheres that describe the surface of the CaM binding and catalytic sites. After searching over the compounds from different chemical libraries, the top 500 compounds that may interact with the EF binding site can be modeled more extensively. After manually modeling the interaction between some of these compounds and EF using a molecular graphics program (MIDAS) and checking for commercial availability, initial candidate compounds can be used to screen the compounds that can block adenylyl cyclase activity either by the enzymatic assays (in vitro or in vivo) or by cell-based assays. Concentration-response curves can be generated to determine the $IC_{50}$ value which will provide an estimate of the affinity of a given inhibitor to EF. Those compounds with µM affinity can be refined by iterative chemical synthesis, testing based on enzymatic activity, and structure determination of EF/CaM/inhibitor complex.

This same technique can also be used for lead optimization. The original hit (such as adenosine or ATP analogs) can be synthesized based on the structures of EF/CaM/ATP complex. Such analogs can be examined for their abilities to inhibit adenylyl cyclase activity of edema factor either by the enzymatic assays (in vitro or in vivo or by cell-based assays. The analysis of structure-activity relationship (SAR) will provide valuable information for chemists to further synthesize the analogs to improve the affinity of lead compounds.

2. Assay Formats to screen for Inhibitors

In certain embodiments, the present invention provides methods for screening and identifying an agent that inhibits the activation of an adenylyl cyclase exotoxin, for example, that stops or decreases EF's adenylyl cyclase activity. Compounds that inhibit the exotoxin's adenylyl cyclase activity can effectively block the increased levels of cAMP in the host cell, thus limiting the negative effects of *Bacillus anthracis, Bordetella pertussis, Pseudomonas aeruginosa,* and/or *Yersinia pestis* on the host cell. This is typically achieved by obtaining the target amino acid site on the adenylyl cyclase exotoxin or the exotoxin/CaM complex, and contacting the amino acid site with candidate agents followed by assays for any change in activity.

Candidate compounds can include fragments or parts of naturally-occurring compounds or may be only found as active combinations of known compounds which are otherwise inactive. In one embodiment, the candidate compounds are small molecules. Alternatively, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

a. In Vitro Assays

The present embodiment of this invention contemplates the use of a method for screening and identifying an agent that inhibits the activation of adenylyl cyclase exotoxins. A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. The target may be either free in solution, fixed to a support, expressed in or on the surface of a cell. Examples of supports include nitrocellulose, a column or a gel. Either the target or the compound may be labeled, thereby permitting determining of binding. In another embodiment, the assay may measure the enhancement of binding of a target to a natural or artificial substrate or binding partner. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564, the disclosure of which is incorporated herein by reference. In high throughput screening, large numbers of candidate inhibitory test compounds, which may be small molecules, natural substrates and ligands, or may be fragments or structural or functional mimetics thereof, are synthesized on a solid substrate, such as plastic pins or some other surface. Alternatively, purified target molecules can be coated directly onto plates or supports for use in drug screening techniques. Also, fusion proteins containing a reactive region (preferably a terminal region) may be used to link an active region of an enzyme to a solid phase, or support. The test compounds are reacted with the target molecule, and bound test compound is detected by various methods (see, e.g., Coligan et al., Current Protocols in Immunology 1(2): Chapter 5 (1991).

Examples of small molecules that may be screened include, but are not limited to, small organic molecules, peptides or peptide-like molecules, nucleic acids, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that inhibit the activation adenylyl cyclase exotoxins. Further, in drug discovery, for example, proteins have been fused with antibody Fc portions for the purpose of high-throughput screening assays to identify potential modulators of new polypeptide targets. See, D. Bennett et al., Journal of Molecular Recognition, 8: 52-58 (1995) and K. Johanson et al., The Journal of Biological Chemistry, 270, (16): 9459-9471 (1995).

b. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that can inhibit the activation of adenylyl cyclase exotoxins secreted by *Bacillus anthracis, Bordetella pertussis, Pseudomonas aeruginosa*, and/or *Yersinia pestis*. In these embodiments, the present invention is directed to a method for determining the ability of a candidate substance to inhibit the activation of the adenylyl cyclase exotoxins secreted by *Bacillus anthracis, Bordetella pertussis, Pseudomonas aeruginosa*, and/or *Yersinia pestis*, generally including the steps of: administering a candidate substance to the animal; and determining the ability of the candidate substance to reduce one or more characteristics of the infection of *Bacillus anthracis, Bordetella pertussis, Pseudomonas aeruginosa*, and/or *Yersinia pestis*

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

c. In Cyto Assays

The present invention also contemplates the screening of compounds for their ability to inhibit the activation of adenylyl cyclase exotoxins secreted by *Bacillus anthracis, Bordetella pertussis, Pseudomonas aeruginosa*, and/or *Yersinia pestis*. Various cell lines can be utilized for such screening assays, including cells specifically engineered for this purpose. Depending on the assay, culture may be required. The cell is examined using any of a number of different assays for screening for adenylyl cyclase activation in the cells.

d. Arrays

Hi-throughput assays, for example, arrays comprising a plurality of ligands arranged on a solid support, represent an important diagnostic tool provided by the invention. The use of arrays involves the placement and binding of nucleic acids, or another type of ligand having affinity for a molecule in a test sample, to known locations, termed sectors, on a solid support.

Arrays can be used, through hybridization of a test sample to the array, to determine the presence or absence of a given molecule in the sample. By including any additional other target nucleic acids or other types of ligands, potentially thousands of target molecules can be simultaneously screened for in a test sample. Many different methods for preparation of arrays comprising target substances arranged on solid supports are known to those of skill in the art and could be used in accordance with the invention. Specific methods for preparation of such arrays are disclosed in, for example, Affinity Techniques, Enzyme Purification: Part B, Meth. Enz. 34 (ed. W. B. Jakoby and M. Wilchek, Acad. Press, N.Y. (1974) and Immobilized Biochemicals and Affinity Chromatography, Adv. Exp. Med. Biol. 42 (ed. R. Dunlap, Plenum Press, N.F. 1974), each specifically incorporated herein by reference in its entirety). Examples of other techniques which have been described for the attachment of test materials to arrays include the use of successive application of multiple layers of biotin, avidin, and extenders (U.S. Pat. No. 4,282,287, specifically incorporated herein by reference in its entirety); methods employing a photochemically active reagent and a coupling agent which attaches the photoreagent to the substrate (U.S. Pat. No. 4,542,102, specifically incorporated herein by reference in its entirety); use of polyacrylamide supports on which are immobilized oligonucleotides (PCT Patent Publication No. 90/07582, specifically incorporated herein by reference in its entirety); use of solid supports on which oligonucleotides are immobilized via a 5'-dithio linkage (PCT Patent Publication No. 91/00868, specifically incorporated herein by reference in its entirety); and through use of a photoactivateable derivative of biotin as the agent for immobilizing a biological polymer of interest onto a solid support (see U.S. Pat. No. 5,252,743; and PCT Patent Publication No. 91/07087 to Barrett et al., each specifically incorporated herein by reference in its entirety). In the case of a solid support made of nitrocellulose or the like, standard techniques for UV-crosslinking may be of particular utility (Sambrook et al., 1989).

The solid support surface upon which an array is produced in accordance with the invention may potentially be any suitable substance. Examples of materials which may be used include polymers, plastics, resins, polysaccharides, silica or silica-based materials, carbon, metals, inorganic glasses, membranes, etc. It may also be advantageous to use a surface which is optically transparent, such as flat glass or a thin layer of single-crystal silicon. Contemplated as being especially useful are nylon filters, such as Hybond N+ (Amersham Corporation, Amersham, UK). Surfaces on the solid substrate will usually, though not always, be composed of the same material as the substrate, and the surface may further contain reactive groups, which could be carboxyl, amino, hydroxyl, or the like.

It is contemplated that one may wish to use a solid support surface which is provided with a layer of crosslinking groups (U.S. Pat. No. 5,412,087, specifically incorporated herein by reference in its entirety). Crosslinking groups could be selected from any suitable class of compounds, for example, aryl acetylenes, ethylene glycol oligomers containing 2 to 10 monomer units, diamines, diacids, amino acids, or combinations thereof. Crosslinking groups can be attached to the surface by a variety of methods that will be readily apparent to one of skill in the art. For example, crosslinking groups may be attached to the surface by siloxane bonds formed via reactions of crosslinking groups bearing trichlorosilyl or trisalkoxy groups with hydroxyl groups on the surface of the substrate. The crosslinking groups can be attached in an ordered array, i.e., as parts of the head groups in a polymerized Langmuir Blodgett film. The linking groups may be attached by a variety of methods that are readily apparent to one skilled in the art, for instance, by esterification or amidation reactions of an activated ester of the linking group with a reactive hydroxyl or amine on the free end of the crosslinking group.

A significant benefit of the arrays of the invention is that they may be used to simultaneously screen for inhibitors of the activation of secreted adenylyl cyclase exotoxins. Use of the arrays generally will comprise, in a first step, contacting the array with a test sample. Generally the test sample will be labeled to facilitate detection of hybridizing test samples. By detection of test samples having affinity for bound target nucleic acids or other ligands, the identity of the target molecule will be known.

Following contacting with the test sample, the solid support surface is then generally washed free of unbound test sample, and the signal corresponding to the probe label is identified for those regions on the surface where the test sample has high affinity. Suitable labels for the test sample include, but are not limited to, radiolabels, chromophores, fluorophores, chemiluminescent moieties, antigens and transition metals. In the case of a fluorescent label, detection can be accomplished with a charge-coupled device (CCD), fluorescence microscopy, or laser scanning (U.S. Pat. No. 5,445,934, specifically incorporated herein by reference in its entirety). When autoradiography is the detection method used, the marker is a radioactive label, such as $^{32}P$, and the surface is exposed to X-ray film, which is developed and read out on a scanner or, alternatively, simply scored manually. With radiolabeled probes, exposure time will typically range from one hour to several days. Fluorescence detection using a fluorophore label, such as fluorescein, attached to the ligand will usually require shorter exposure times. Alternatively, the presence of a bound probe may be detected using a variety of other techniques, such as an assay with a labeled enzyme, antibody, or the like. Detection also may, in the case of nucleic acids, alternatively be carried out using PCR. In this instance, PCR detection may be carried out in situ on the slide. In this case one may wish to utilize one or more labeled nucleotides in the PCR mix to produce a detectable signal. Other techniques using various marker systems for detecting bound ligand will also be readily apparent to those skilled in the art.

III. Immunological Detection

1. Immunoassays

Immunoassays may find use with the invention in certain prognostic/diagnostic applications that comprise assaying for the presence of the adenylyl cyclase exotoxin and/or the exotoxin-CaM molecule. As indicated above, such immunoassays specifically include the use of hi-throughput techniques including use of arrays. The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample containing a target protein or peptide, and contact the sample with an antibody, as the case may be, and then detect or quantify the amount of immune complexes formed under the specific conditions.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as the EF protein or the EF-CaM molecule as seen in Bacillus anthracis. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference.

The immunodetection methods of the present invention have evident utility in the diagnosis anthrax. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

IV. Therapeutic Application of the Invention

The current invention provides methods and compositions for the inhibition of the activation of adeneylyl cyclase exotoxins secreted by *Bacillus anthracis, Bordetella pertussis, Pseudomonas aeruginosa*, and/or *Yersinia pestis*. The invention therefore provides therapies to treat these bacterial infections, for example, by administering a pharmaceutical composition comprising an inhibitor of the activation of the adenylyl cyclase exotoxin secreted by *Bacillus anthracis, Bordetella pertussis, Pseudomonas aeruginosa*, and/or *Yersinia pestis*. Administration may be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection.

V. Pharmaceutical Compositions and Dosages

Pharmaceutical compositions of the present invention comprise an effective amount of one or more inhibitors of the activation of adeneylyl cyclase exotoxins secreted by *Bacillus anthracis, Bordetella pertussis, Pseudomonas aeruginosa*, and/or *Yersinia pestis* or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one inhibitor of adenylyl cyclase activity or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated.

The inhibitors of the activation of adeneylyl cyclase exotoxins may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The inhibitors of the activation of adeneylyl cyclase exotoxins may be formulated into a composition in a free base, neutral or salt form. Pharmaceutically acceptable salts, include the acid addition salts, e.g., those fonned with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the inhibitors of the activation of adeneylyl cyclase exotoxins are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

EXAMPLES

Example 1

General Description of the EF structure with and without CaM

The structure of EF-CaM at 2.75 Å resolution was solved using selenomethionine multiple wavelength anomalous diffraction (MAD) in conjunction with conventional heavy atom methods (Drum et al., 2001) (Table 1). The structure of EF without CaM or substrate at 2.6 Å resolution was solved by molecular replacement using the catalytic core domains of EF-CaM/3-d'ATP as the model. Crystals of the EF-CaM complex in the absence of the nucleotide substrate were isomorphous with those of the 3'-dATP-bound CaM complex. The R-factors for EF alone, EF-CaM-3'dATP, and EF-CaM are 22.8%($R_{free}$=27.6%), 21.5%(28.6%), and 27.8%(31.5%), respectively.

TABLE 1

Crystallographic and refinement statistics

A. Crystallographic data

| Crystal | EF3-CH$_6$-CaM-3'dATP | H$_6$-EF3 | EF3-CH$_6$-CaM |
|---|---|---|---|
| Space group | I222 | P2$_1$2$_1$2 | I222 |
| a | 117.60 | 50.47 | 116.73 |
| b | 167.44 | 203.60 | 167.31 |
| c | 343.48 | 74.03 | 344.30 |
| X-Ray source | APS, 14-BM-C | APS, 14-BM-C | NSLS X-25 |
| Resolution (Å) | 2.75 | 2.6 | 2.95 |
| completeness (%) (last shell) | 91.6 (57.2) | 98.5 (95.4) | 98.8 (98.1) |
| R-sym (last shell) | 9.7 (26.4) | 8.7 (27.3) | 6.1 (26.6) |
| I/σ (last shell) | 4.6 (2.8) | 5.6 (1.7) | 18.5 (4.1) |
| Redundancy (last shell) | 10.9 (3.3) | 6.5 (4.8) | 16.0 (5.5) |

B. Refinement

| Resolution (Å) | 20-2.75 | 30-2.6 | 30-2.95 |
|---|---|---|---|
| R-factor/free (%) | 21.5/28.6 | 22.8/27.6 | 27.8/31.5 |
| Bond length (Å) | 0.005 | 0.011 | 0.011 |
| Bond angle (degree) | 1.8 | 1.55 | 1.6 |

Figure 2:
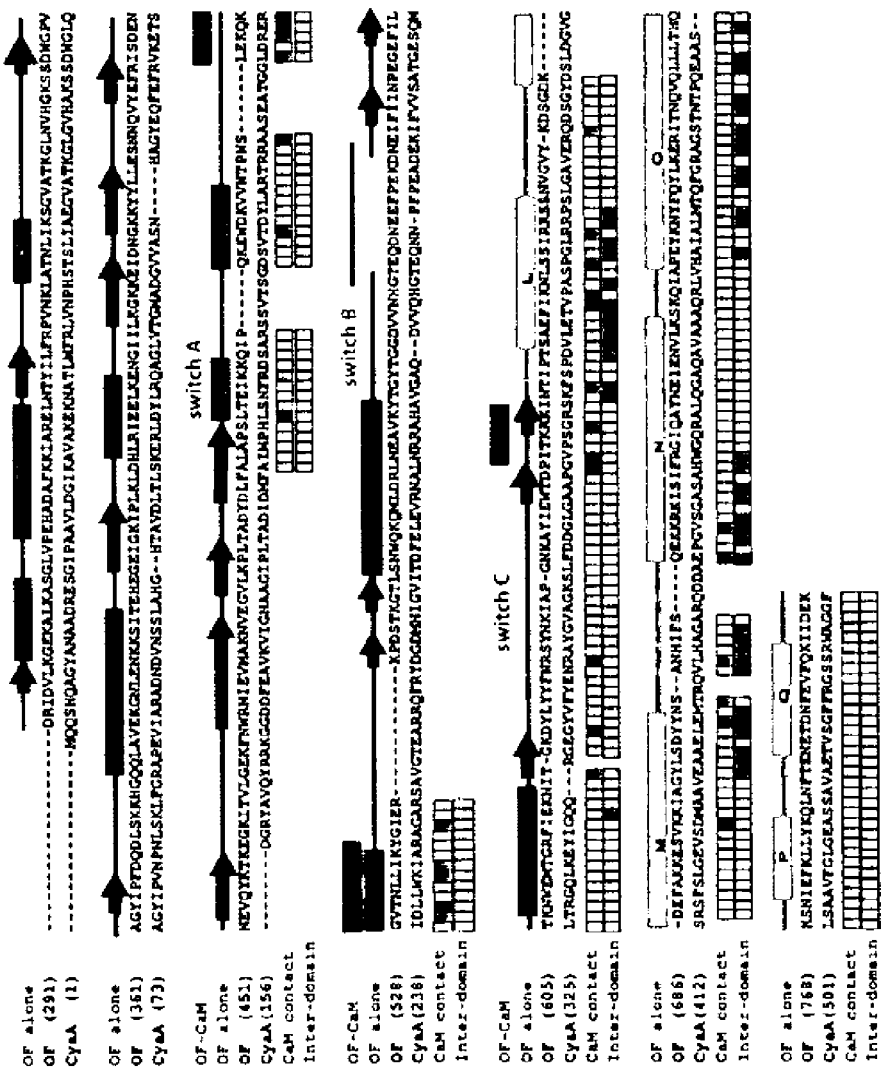
FIG. 2 Sequence alignment of EF (SEQ ID NO. 1) and CyaA (SEQ ID NO. 2). On the top of sequence shows the second structure assignment of EF alone. The second structures of EF-CaM that differ from EF alone are shown on the top of EF alone structure when applicable. Residues that contact the nucleotide substrate are highlighted red. Molecular contacts are shown as the colored boxes below the sequences. CaM contact residues are colored in five shades of red. These residues are colored in 20 Å$^2$ increments, based on their CaM contact area. The lightest colored boxes indicate less than 20 Å$^2$ of contact area, the darkest colored boxes indicate that more than 80 Å$^2$ are buried by the CaM interaction. Inter-domain indicates residues that are involved inter-domain interaction between the helical domain and the remainder of EF in the EF alone structure. They are colored based on their contact region including switch A (cyan), switch C (magenta), $C_A$ region (green), and helical domain (yellow). /////
Figure 3:
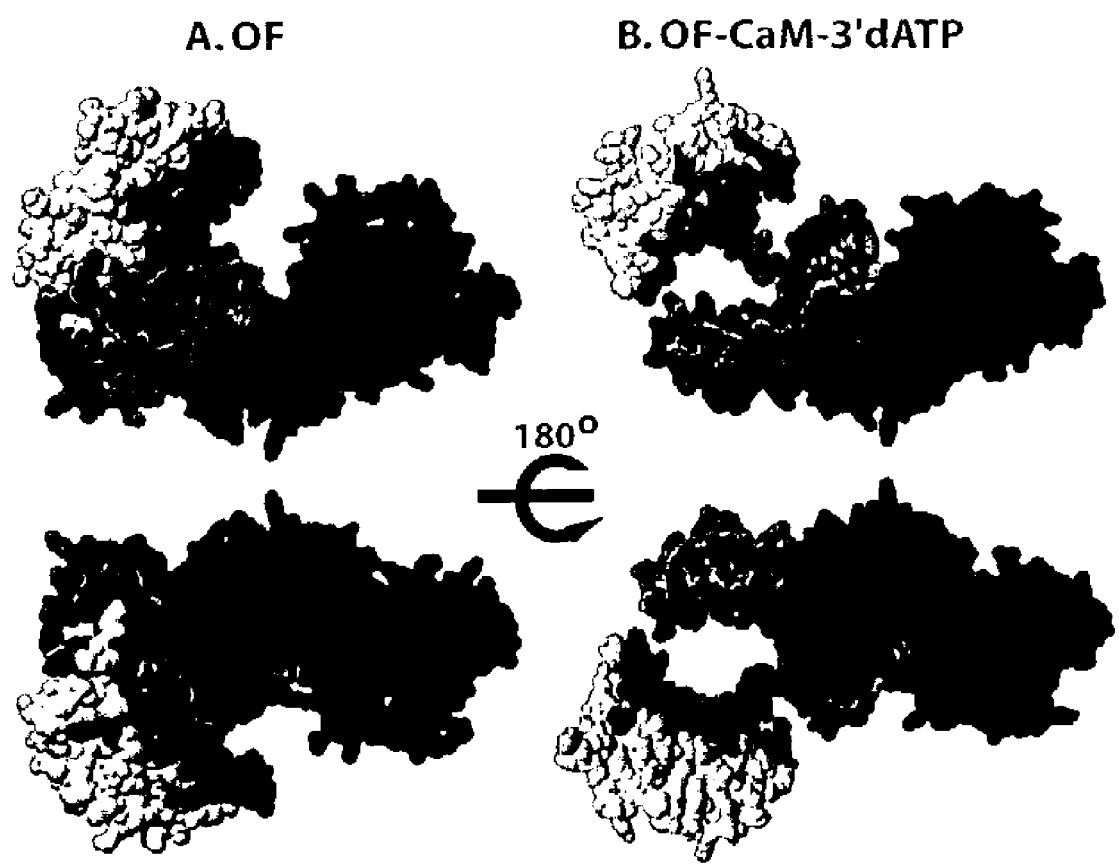
FIG. 3A and FIG. 3B Space filling representation of EF alone FIG. 3A and CaM-complexed EF FIG. 3 B. Switch A, B and C atoms are colored cyan, orange, and yellow, respectively. Residues which contact CaM are red.

The structure of EF alone differs significantly from that of EF-CaM. There are, however, essentially no differences between the structures of EF-CaM with and without nucleotide (FIG. 1A and FIG. 1B). Thus, the differences between EF alone and EF-CaM are almost entirely CaM-induced. The catalytic portion of EF is composed of three globular domains (FIG. 1A, FIG. 1B, and FIG. 2). The active site lies at the interface of two domains, C$_A$ (a.a. 294-349 and 490-622) and C$_B$ (a.a. 350-489), which together constitute the catalytic core. A third, helical domain (residues 660-800), is connected to C$_A$ by a linker (residues 623-659). In the structure of EF alone, the interface between the helical domain and the remainder of the protein buries 16 hydrophobic residues and 3600 Å$^2$ of surface area. None of these interactions are preserved in the EF-CaM complex, however, since CaM inserts itself between C$_A$ and the helical domain. In doing so, CaM occupies much of the same volume occupied by the helical domain in the structure of EF-alone. To accommodate CaM, the helical domain, acting as a unit, moves 15 Å and rotates 30°, such that C$_A$, the linker, and the helical domain now form a large clamp which almost completely encircles the activator. There are no contacts between C$_A$ and the helical domain in the EF-CaM structures, but residues from these domains approaching from either side of CaM come within 5.6 Å of one another at the tip of the clamp (FIG. 3A, and FIG. 3B). The CaM interface buries 2950 Å$^2$ and 2912 Å$^2$ of solvent accessible surface area on EF and CaM, respectively.

Figure 4:
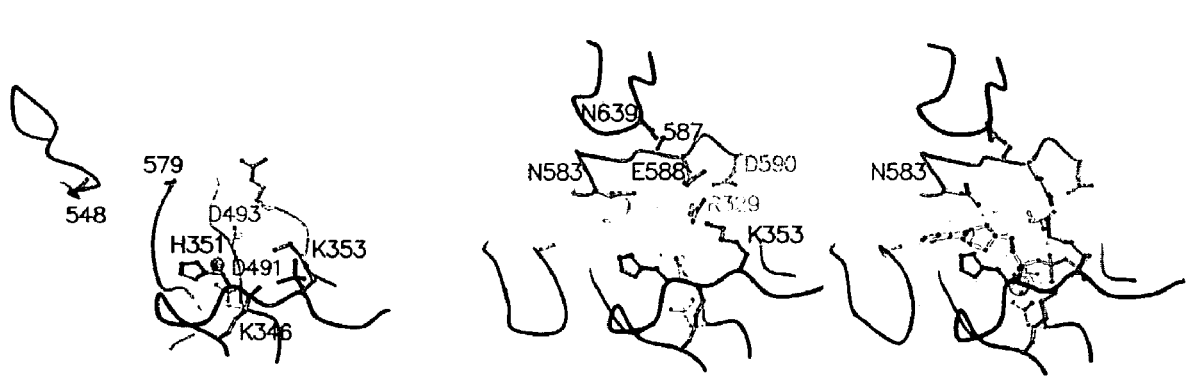
FIG. 4A, FIG. 4B, and FIG. 4C Switch movement results in catalytic activation. This view looks down from the top of the molecule relative to FIG. 1.

In addition to the helical domain movement, three regions designated as switch A, B and C undergo large conformational changes in response to CaM binding (FIG. 1A, FIG. 1B, FIG. 4A, FIG. 4B, and FIG. 4C). Switch A and C are the predominant regions that interface with the helical domain in the EF-alone structure, thus they have a large movement to accommodate the insertion of CaM (FIG. 2). Switch A (a.a. 502-551) includes residues that bind CaM and nucleotide. In the EF-alone structure, this loop is nestled on the side of domain C$_A$ and its tip is 20 Å away from its active state position. Switch C (a.a. 630-659) is composed of residues from the linker that connects C$_A$ to the helical domain. This region undergoes the largest structural change within EF. The tip of the Switch C loop swings 33 Å from its position near the active site in EF-CaM to the opposite side of the enzyme in EF alone. Within switch C, residues 642-652 are converted from two β-strands and a connecting loop to a helix in the EF-CaM structure (residues 648-653). Switch B (a.a. 578-591), which makes several specific contacts with the substrate in EF-CaM, becomes disordered when CaM is not present. This disorder cannot be attributed to the lack of substrate in the EF-alone structure since these residues are clearly visible in the structure of substrate-free EF-CaM (FIG. 4B). Switch B also makes extensive contacts with switch C in the EF-CaM complex. Outside of the helical domain and the three defined switches, the remaining residues are relatively unchanged.

Example 2

Geometry of the Active Site of EF-CaM Complex

Figure 5:
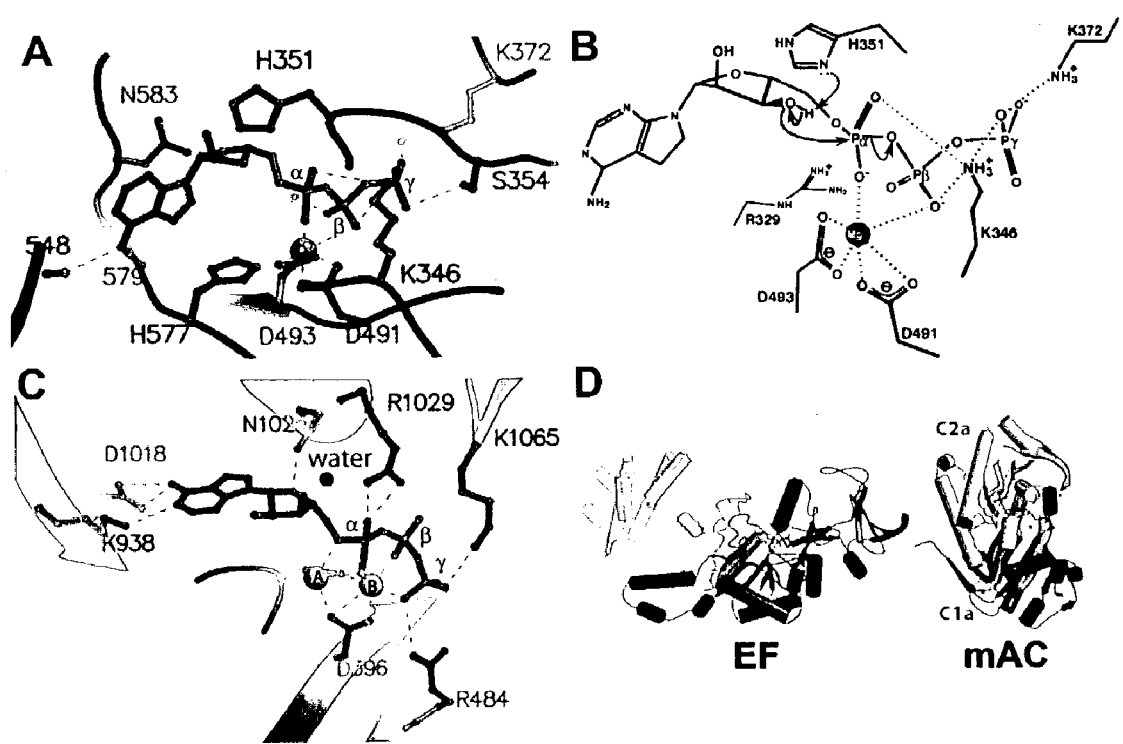
FIG. 5A, FIG. 5B, FIG. 5C, and FIG. 5D Active site of EF and its comparison with mAC.

3'dATP, a non-cyclizable substrate analog, is clearly visible in simulated annealing omit maps of the EF-CaM-3'dATP structure (supplemental material). Residues from six segments of the protein form the substrate-binding pocket (FIG. 5A). These residues form a network of hydrogen bonds and ionic interactions, which completely encircle the triphosphate and ribose moieties, forming an enclosed cavity with openings at both ends (FIG. 5A). The most notable phosphate interactions are made by K346, which contacts oxygens from all three phosphates; R329, which interacts with the β-phosphate; and K372 and S354, which interact with the γ-phosphate (FIG. 5A). F586 and L348 lie above and below the plane of the ribose, and the side chain of N583 forms a hydrogen bond with O4' of the ribose ring. The adenosine ring, though solvent accessible, contacts the backbone of D582 and N583, and the N6 nitrogen is within hydrogen bonding distance of the main chain carbonyls of T579 and T548. Mutational analysis of many of these residues supports their importance in catalysis (table 2) (Drum et al., 2000).

TABLE 2

Calmodulin activation of wild type and mutant forms of EF[a]

|  | V$_{max}$(s$^{-1}$) | EC$_{50}$(nM) | K$_M$(mM) | V$_{max}$/K$_M$ |
|---|---|---|---|---|
| EF | 11970 | 1.3 | 0.21 | 57000 |
| K346R | 0.05 | 32.0 | 0.55 | 0.09 |
| K353R | 812 | 0.8 | 0.47 | 1728 |
| K353A | 20 | 1.0 | 1.38 | 15 |
| L523A | 5590 | 1.3 | 0.21 | 26571 |
| K525A | 2490 | 256.0 | 0.26 | 9577 |
| Q526A | 6980 | 1.9 | 0.25 | 27920 |
| V529A | 4360 | 1.8 | 0.28 | 15571 |
| H577N | 65 | 6.1 | 0.28 | 232 |
| H577D | 0.24 | 8.0 | 0.31 | 0.77 |
| N583A | 84 | 3.3 | 0.52 | 162 |
| N583Q | 21 | 1.6 | 0.72 | 29 |
| N583H | 58 | 1.5 | 0.86 | 67 |
| E588A | 501 | 1.1 | 0.63 | 785 |
| D590A | 1880 | 1.1 | 0.79 | 2380 |
| N639A | 950 | 2.0 | 0.30 | 3167 |
| D647A | 40 | 0.7 | 0.41 | 98 |

[a]The adenylyl cyclase assay was performed with EF, K353R, E588A, D590A, L523A, K525A, Q526A, V529A (5 ng), K353A, H577N, H577D, N583A, N583Q, N583H, N639A, D647A (50 ng), and H577N, K346R (15 μg) at 30° C. for 10 min in the present of 5 mM ATP, 10 mM MgCl$_2$ and 0.05 mM CaCl$_2$. EC$_{50,CaM}$ was determined using CaM concentration ranging from 0.01 to 1000 nM in 3.1 or 10 fold increments and the results were fit to into a simple rectangular hyperbola. K$_{M,ATP}$ was determined using ATP concentrations ranging from 0.06 to 2 mM in 2 fold increments and the results were fit in the same way. These data are representative of at least two experiments. These data are representative of at least two experiments.

At the base of the cleft formed by domains C$_A$ and C$_B$, a single metal interacts with the oxygens of the alpha and beta phosphates of 3'-deoxy ATP. This metal is coordinated by two conserved aspartates, D491 and D493. Mutation of either aspartic acid in EF and its homologs CyaA, and ExoY (exotoxins from *Bordetella pertussis* and *Pseudomonas aeruginosa*, respectively) results in catalytic inactivation of the enzyme (FIG. 2) (Yahr et al, 1998; Drum et al., 2000; Glaser et al., 1991). Based on the strength of the electron density and the anomalous scattering signal, we believe the metal present in our highest resolution data set is $Yb^{2+}$, an additive used to improve crystal quality. This $Yb^{2+}$ is at the presumed position of the catalytic $Mg^{2+}$, which interacts with the α- and β-phosphates of the substrate. Though Yb and Mg ions were both present in the crystallization mixture, no metal ion was found in the catalytic site of EF-CaM in the absence of ATP analog (FIG. 4B). This suggests that the presence of substrate may be required for binding of the catalytic metal ion. However, based on the anomalous scattering signal, a $Ni^{2+}$ ion is coordinated by D491 and D493 in the catalytic site of the EF alone structure (FIG. 4A). Since diffracting crystals of EF alone were only obtained at high $NiSO_4$ concentration (220-280 mM), the physiological relevance of this metal ion found in the catalytic site remains unclear.

H351 lies on the opposite side of the ribose from the metal and is well positioned to interact with the reactive 3'OH when the ribose is in the 3'-endo conformation observed in the crystal (FIG. 5A). The homologous histidine in CyaA, H63, has been shown to act as a catalytic base (Munier et al., 1992). Though the 3' hydroxyl is absent from the nucleotide analog used in this study, the expected position of this atom is generally consistent with that required for in-line nucleophilic attack on the α-phosphate. In this reaction scheme, the metal, along with K346, would serve to activate the α-phosphate and stabilize the developing charge on the oxygen bridging the α- and β-phosphates (FIG. 5B). This catalytic mechanism differs from that proposed for mammalian adenylyl cyclases (mAC), which are thought to utilize a two-metal-ion catalysis. Whereas H577 appears to be positioned such that it could coordinate a second metal ion in conjunction with D493, mutational analysis argues against such a role (Table 2). H577N has 250-fold higher catalytic activity than H577D, a mutation that would favor the binding of second metal ion.

Example 3

Comparison of EF and Mammalian Adenylyl Cyclase

Four genetically unrelated groups catalogue all known adenylyl cyclases. While the catalytic core structures of mAC and ESAG from *Trypanosoma brucei* (class III, the family of adenylyl cyclases from bacteria to mammals (Tang and Hurley, 1998) have been determined crystallographically (Tesmer et al., 1997; Bieger and Essen, 2001), EF represents the first member of the adenylyl cyclase toxin family (class II) to be structurally characterized. Comparison of these two classes reveals no obvious structural homology (FIG. 5D). Whereas the catalytic portion of the mammalian enzymes is composed of two similarly folded domains, C1a and C2a, with rough two-fold symmetry; EF, which functions as a soluble monomer, has no such symmetry. Superimposing the ATPaS nucleotide from mAC with the 3'dATP nucleotide seen in EF-CaM reveals that despite a lack of overall structural homology, there are residue-level similarities in substrate binding and catalysis between these two enzyme families (FIG. 5A and FIG. 5C) (Tesmer et., 1997). Both enzymes have an asparagine (N583 of EF and N1025 of mAC) that forms a hydrogen bond to the O4' of the ribose ring and could serve to position the ribose. Both enzymes also have a cluster of positively charged residues (R329, K346, K372 of EF and R1029, K1065, and R484 of mAC), which could serve to stabilize the pentavalent transition state formed during catalysis. In addition, both enzymes contain a catalytically required metal ion, which is held in position by two aspartates (D491 and D493 of EF and D396 and D440 of mAC). These similarities do not extend beyond the immediate vicinity of the catalytic center, with structural divergence seen even in the contacts stabilizing the adenine rings (FIG. 5A and FIG. 5C).

The mechanism whereby EF and mAC generate the attacking 3' O— is also 10 different (FIG. 5A and FIG. 5C). In EF, H351 appears to serve as a catalytic base, removing the proton from the 3'OH. mACs and their relatives do not have a conserved histidine in their catalytic site, and are thought to use a second metal ion for this purpose (Tesmer et al., 1999). mACs have structural homology to the catalytic "palm domains" of the oligonucleotide polymerase family, a family known to use two-metal-ion catalysis (Tesmer et al., 1999). Supporting the assertion that mACs work like polymerases, a second metal ion (ion A), adjacent to the first (ion B), has been observed in the structure of zinc-complexed mAC (Tesmer et al., 1999). Substitution of the metal at site A with a histidine for deprotonation is not unprecedented. Most restriction endonucleases (which catalyze destruction rather than formation of a phosphodiester bond) use two-metal-ion catalysis, however two homing endonucleases, I-PpoI and Serratia nuclease, are known to have a histidine for deprotonation instead of a site A metal (Galburt et al, 1999; Miller and Krause, 1999).

The ribose in the structure of mAC/ATPocS is oriented such that the 3'OH is too far for effective deprotonation from metal ion A (5.3 Å) (FIG. 5C) (Tesmer et al., 1999). As the ribose in the mAC structure is oriented similarly to that seen in EF, an alternative mechanism of catalysis can be proposed. In the structure of mAC, a well-ordered water molecule, 3 Å from the 3'OH of ATPαS, forms a hydrogen bond with the hydroxyl group of serine 1028 (FIG. 5C). This water molecule is also 3 Å from the amino group of R1029, a conserved residue that is crucial for catalysis (Yan et al., 1997). Were this "water" a hydroxide anion, stabilized by the nearby arginine, it could serve as a base to draw the proton from the 3'OH. Alternatively, R1029, with its amino group is 3.5 Å away from 3'OH, might serve to stabilize 3' O⁻ or act as a catalytic base directly.

Example 4

CaM Binding of EF

CaM adopts an extended conformation when bound to EF. The distance between the two CaM lobes is similar to that observed in the crystal structure of extended, $Ca^{2+}$-bound calmodulin (Babu et al., 1985). However, the EF interaction causes residues 79-81 of the central helix to unwind, and causes the N-terminal CaM lobe to rotate by 80° with respect to the $Ca^{2+}$-bound crystal structure (FIG. 1A and FIG. 1B). Unwinding of the CaM central helix is not surprising as this region is flexible in solution and is readily unfolded upon target binding (Lewit-Bentley and Rety, 2000). In the EF-CaM structure, the C-terminal domain of CaM binds two calcium ions and is similar to that seen in previous $Ca^{2+}$-loaded CaM structures (rmsd 0.62 Å over 61 amino acids) (Babu et al., 1985). Consistent with biochemical data, the N-terminal lobe adopts a calcium-free conformation (rmsd 1.2 Å over 67 amino acids) (Drum etal., 2000; Zhang et al., 1995).

Figure 6:
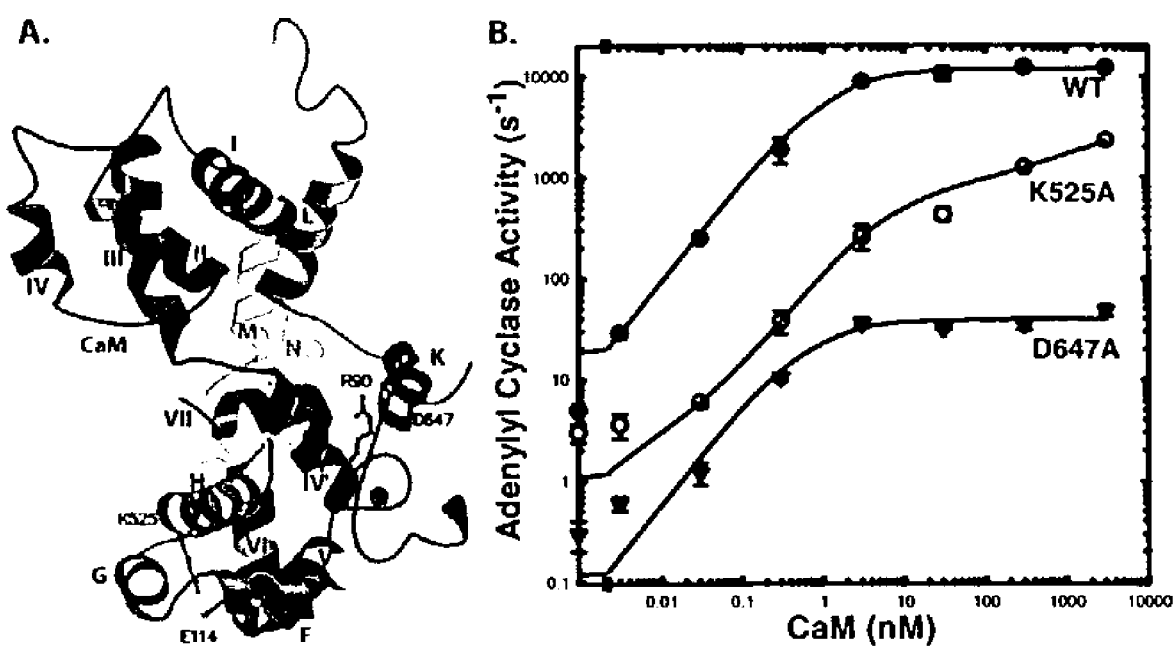
FIG. 6A and FIG. 6B CaM binding of EF. This view is rotated 90° relative to FIG. 1.

Calcium-binding EF-hand domains undergo a variety of interactions with other proteins (Meng et al., 1998; Huang et al., 2000). The structure of EF-CaM suggests that CaM can also use an extensive repertoire of conformations and interactions as it regulates its many targets. An intricate network of hydrophobic and hydrophilic contacts appears to be responsible for the tight binding constant between EF and CaM ($K_d$=20 nM) (Drum et al., 2000). Excluding residues with less than 10 Å² of contact area, 63 predominantly hydrophobic and basic EF residues contact 53 residues from CaM (FIG. 2). These contacts are divided among two segments of the EF sequence; residues 501-540, which are part of domain $C_A$, and residues 616-798, which correspond to switch C and the helical domain. The first segment was previously identified as a CaM binding domain, and this region has also been identified in CyaA (Munier et al., 1995). This first segment interacts with CaM helices IV, V, and VI, and, as discussed below, part of this segment is structurally similar to other CaM-target interactions (FIG. 6A). The latter segment consists of multiple CaM/effector binding surfaces, and the interaction of this part of EF with CaM is consistent with cross-linking data (Labruyure et al., 1990). Within this latter region, there are three discrete CaM binding segment (residue 615-634, 647-672, and 695-721) to form extensive contacts with three out of four EF-hand domains in CaM (FIG. 2 and FIG. 6A). The EF helices L and M make significant contacts to the first EF hand domain of CaM which appears to stabilize the $Ca^{2+}$-free conformation observed in the N-terminal CaM lobe.

Example 5

Activation of EF by CaM

The adenylyl cyclase domain of EF is basic, with a calculated pI of 9.0. In the EF alone structure, $C_A$, the helical domain and switch C form a contiguous, positively charged surface which is likely to be a driving force in attracting the highly negatively charged CaM (pI=3.9). The affinity of the helical domain for the enzymatic core is likely to be a primary energetic obstacle to EF activation. The unusually large binding surface between EF and CaM, however, may serve to generate enough free energy to simultaneously allow high affinity CaM binding and to stabilize the structural rearrangements which activate EF. All four CaM binding regions of EF are partially buried (FIG. 4A, FIG. 4B, FIG. 4C, FIG. 5A, FIG. 5B, FIG. 5C and FIG. 5D). The inventors use alaninescan mutagenesis to characterize the order of CaM binding to two of these four regions (FIG. 6A). In the EF-CaM structure, the amino group of K525 within helix H forms a 4.0 Å salt bridge with the carboxyl group of CaM residue E114 (FIG. 6A). In EF alone structure, K525 is largely exposed. The K525A mutation drastically increases the $EC_{50}$ value (200 fold) with only a small reduction in $V_{max}$ (FIG. 6B and Table 2). The mutations in nearby residues L523, Q526, and V529 result in minimal changes in CaM activation (Table 2). These data indicate that helix H is important for the initial binding of EF to CaM with K525 being a binding hot spot.

Switch C is immediately connected to the helical domain and undergoes the largest conformational change upon CaM binding. Its C-terminal portion (a.a. 646-659) interacts extensively with helices IV' and VII and the third calcium binding loop of CaM. Most noticeably, the carboxyl group of D647 forms a salt bridge with the guanido group of R90 from CaM (FIG. 6A). In the EF alone structure, D647 is mostly buried and forms a network of hydrogen bonds with the hydroxyl group of S669 and amide groups of P648 and 1649. Thus, the interaction of D647 with CaM is likely to occur after the conformational change of switch C induced by the initial binding of CaM. The mutation of D647 to alanine is consistent with this notion. D647A has a significant reduction in the $V_{max}$ value for CaM activation while its $EC_{50}$ value has little change (FIG. 6B and Table 2).

In the EF alone structure, switch B is disordered, but it becomes highly ordered in the EF-CaM complex (FIG. 4A, FIG. 4B, and FIG. 4C). This transition is most likely due to the extensive contacts between switch B and the N-terminal portion of switch C (aa 631-644). Noticeably, the amide group of N639 forms hydrogen bonds with the main chain carbonyl of P587. Consequently, the mutation of N639 to alanine results in a 12-fold reduction in the rate of catalysis (FIG. 4C, Table 2).

Switch B (a.a. 579-591) contains several residues that either bind ATP directly or stabilize the catalytic residues (FIG. 3A and FIG. 3B). The main chain carbonyl of T579 forms hydrogen bonds with N6 of the adenine base, and the amide group of N583 forms a crucial interaction with the ribose. Mutating N583 to alanine causes a 180-fold reduction in catalytic activity (FIG. 4C, Table 2). Substitutions of N583 to other hydrogen-bond forming residues such as glutamine and histidine result in greater than 400 fold reduction, highlighting the importance of the precise stereochemistry of the N583 side chain (FIG. 4C, Table 2). ATP is locked into the catalytic site by a salt bridge formed between the carboxyl group of E588 and the amino group of K353. Mutations of either residue result in a significant reduction in the catalytic activity (FIG. 4C, Table 2). In addition, the carboxyl group of D590 forms a salt bridge with the guanido group of R329, which interacts with the ATP β-phosphate. R329 participates directly in catalysis, and the mutation of D590 results in more than 20 fold reduction in the value of $V_{max}/K_M$ (FIG. 4C, Table 2).

Example 6

Comparison to CaM Binding and Activation of Other Target Enzymes

EF is homologous to CyaA which is an exotoxin secreted by *Bordetella pertussis* (Ladant and Ullmann, 1999). In addition to its N-terminal adenylyl cyclase domain however, CyaA, a 1705 a.a. protein also contains residues responsible for hemolytic activity. Despite an overall sequence identity of only 24%, the residues around the active site are highly conserved between EF and CyaA (FIG. 2). Only two out of fifteen residues that contact the substrate differs between two proteins and these two residues use their main chain, rather side chain atoms to contact the substrate. The conformation of CaM when complexed to EF and CyaA are most likely similar, as both proteins lead to reduced quenching (indicating an extended CaM structure) in a fluorescence resonance energy transfer (FRET) experiment utilizing a CaM mutant having a fluorescence donor (AEDANS) on one lobe and a non-fluorescence acceptor (DAB) on the other (Supplemental material) (Drum et al. 2000). The Kd of CyaA (residue 1-412) for CaM obtained from fluorescence titration was 10 μM.

Figure 7:
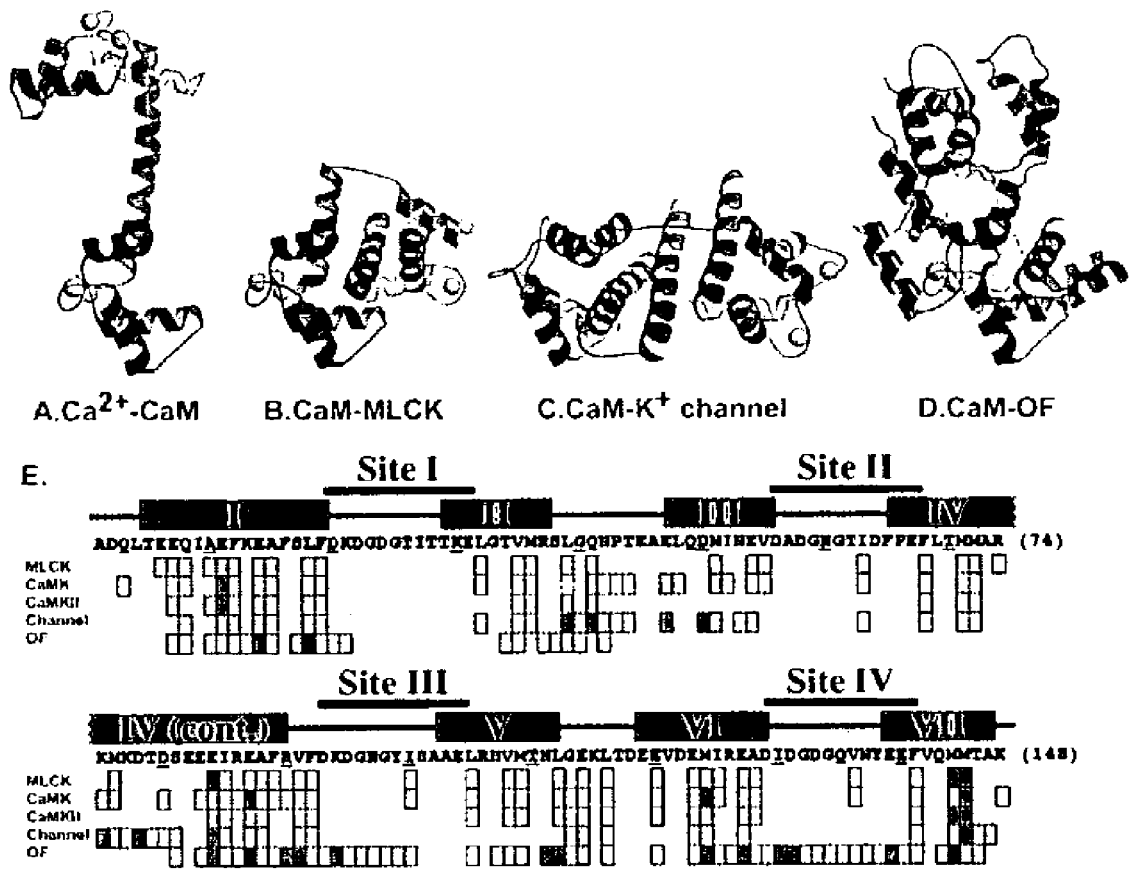
FIG. 7A, FIG. 7B, FIG. 7C, FIG. 7D, and FIG. 7E Comparison of CaM conformations and of CaM/effector contacts.

The crystal structures of CaM in complex with fragments from myosin light chain kinase (MLCK) (Meador et al., 1992), CaM kinase II α (CaMKIIα) (Meador et al., 1993), CaM kinase kinase (CaMKK)(Osawa et al., 1999) and the $Ca^{2+}$-sensitive potassium channel (Schumacher et al., 2001) define the canonical view of CaM/effector interaction in which the hydrophobic faces of the two CaM lobes act as a clamp, surrounding a target helix or helices (FIG. 7B and FIG. 7C). The structure of the EF-CaM complex differs dramatically from this view. In the EF-CaM complex, the calmodulin lobes do not serve as a clamp. The overall conformation of calmodulin is extended rather than compact, and the hydrophobic binding surface of the calcium-free N-terminus is buried within CaM rather than oriented towards the effector target. In spite of these differences, the interaction between the C-terminal lobe of CaM and EF helix H, which harbors 22% of the total CaM-binding surface, is very similar to the interaction observed with recognition helix peptides from MLCK, and CAMKII (Meador et al., 1992; Meador et al., 1993).

Because peptides derived from a number of CaM binding proteins have been used previously to probe the structure of CaM in complex with various CaM-effectors (Meador et al., 1992; Meador et al., 1993; Osawa et al., 1999), the inventors tested the effect of an EF helix H peptide on the conformation of CaM in isolation of the surrounding EF enzyme using the aforementioned FRET technique. The entire catalytic domain of EF causes a decrease in energy transfer efficiency, indicating an extended CaM conformation (Drum et al., 2000). However, a helix H peptide (residues 521-539) causes increased energy transfer similar to an MLCK peptide, indicating a more compact conformation (supplemental material). The apparent dissociation constant of helix H peptide obtained from the titration data was 8.8 µM, indicating ~1000 times weaker affinity than that of intact enzyme. Nonetheless, CaM does interact with the helix H peptide of EF, and the conformation of CaM induced by this peptide clearly differs from the structure of CaM when it is bound to intact EF protein.

Rhoades and Friedberg (Rhoads and Friedberg, 1997) have cataloged over 50 CaM effector molecules based on the presence of positively charged amino acids and characteristic 1-5-10 or 1-8-14 pacings of hydrophobic residues within putative CaM-binding helices. EF was identified as having a 1-8-14 motif, but in the crystal structure the amino acids with this spacing do not interact with CaM. EF helix H contains a 1-5-10 spacing of hydrophobic residues (V529, L533, I538), but these residues are three amino acids out of register when structurally superimposed with the 1-5-10 motif observed in the crystal structure of CaM in complex with a CaMKII peptide. Taken together with our FRET data, these observations underscore the difficulty in predicting CaM conformation and CaM interaction with its targets based on sequence homology and peptide studies.

Similar to EF, CaM makes multiple contacts to several CaM effectors such as ion channels, MLCK, glycogen phosphorylase kinase, Smad, and brush border myosin I (Schumacher et a.l, 2001; Pitt et al., 2001; Krueger et al., 2001; Swanljung-Collins, 1991; Scherer and Graff, 2000; Trewhella et al, 1990). The structure of the complex of CaM and the gating domain of the $Ca^{2+}$-activated $K^+$ channel reveals that two CaM binding sites within the channel allow CaM to induce the dimerization of the channel to trigger calcium-induced activation (FIG. 7C) (Schumacher et al., 2001). Studies involving caldesmon, phosphorylase kinase, and CAP-23/NAP-22 have implied interactions outside of the classically defined CaM binding surfaces (Trewhella et al., 1990; Farrar et al, 1993; Hayashi et al., 2000; Wang et al., 1997). Recent X-ray scattering data show that in addition to the conventional contact surfaces, the N-terminal end of CaM binds to the C-terminal end of the MLCK catalytic core in order to remove the inhibitory domain of MLCK (Krueger et al., 2001).

Removal of an auto-inhibitory domain, through conformational changes induced by CaM, is a prevalent mechanism for CaM activation of its targets, including a family of kinases, calcineurin, nitric oxide synthase, and phosphodiesterase (Eldik and Watterson, 1998). Consequently, the truncation mutants of these proteins lacking an inhibitory domain are constitutively active (Eldik and Watterson, 1998; Montgomery et al., 2000). Although CaM binding displaces the EF helical domain from a catalytic core, the EF helical domain does not serve as an inhibitory domain. EF without the helical domain is catalytically inactive and less sensitive to CaM activation (Drum et al., 2000). Instead, movement of the EF helical domain from a catalytic core triggers reorientation of switch C which leads to the stabilization of a catalytic loop, switch B.

Example 7

Discussion of Activation of EF by CaM

Anthrax has long been a model for understanding the epidemiology and basic biology of infectious disease (Dixon et al., 1999). When Koch outlined the standard criteria with which to define an infectious agent, *Bacillus anthracis* was the first model organism that met all of 'Koch's Postulates'. Subsequently, Louis Pasteur formed the first recorded vaccine by heating anthrax spores and inoculating livestock. Given the historical importance of prokaryotic toxins to our current understanding of eukaryotic biochemistry, it is fitting that an anthrax protein should help shape our thinking about CaM, one of the most ubiquitous and conserved proteins in vertebrate biology. The structure of EF-CaM is the first instance where a functional effector/CaM entity has been characterized structurally, and the complex has the largest protein-protein interface observed to date (Conte et al., 1999). This study using a combination of structural and biochemical analyses suggests a detailed molecular mechanism for how CaM binds four discrete domains of EF to displace a helical domain and consequently stabilize a catalytic loop. Such understanding of the mechanism in CaM activation of EF gives the first molecular insight into how CaM activates a target. Future structural studies of effector/CaM complexes are likely to unveil a rich repertoire of CaM/effector interactions.

There are a variety of mechanisms whereby activators are known to activate enzymes. In the case of GTPase activating protein of low molecular weight G proteins, the activator contributes catalytic residues directly to the active site (Nassar et al., 1998; Rittinger et al., 1997; Scheffzek et al., 1997). In the case of mammalian adenylyl cyclases, the a subunit of Gs, acting from a distance, stabilizes the assembly of a two-part active site (Tesmer et al., 1999). In the case of CaM kinase/CaM, an autoinhibitory peptide is removed from the active site (Eldik and Watterson, 1998). The activation of EF by CaM may be thought of as an extreme example of yet another activation mechanism; that seen in the activation of GTPase activity of Gα proteins by RGS (Tesmer et al., 1997). In this case, the catalytic machinery is present near the site of catalysis, but is disordered in the inactive state. The most surprising aspect of EF activation by CaM is the fact that the conformational switches associated with activation do not involve residues that participate in catalysis. The catalytic base, the metal binding site, and all of the amino acids thought to be involved in stabilizing the pentavalent transition state are virtually identical in the active and inactive states of the enzyme. Furthermore, these residues are significantly more exposed to solvent (and substrate) in the inactive state than in the active state. The inventors structural and biochemical work indicates that the switch that gives rise to 1000 fold enzyme activity involves residues which bind and position the substrate, not those that perform the catalytic reaction.

EF-like adenylyl cyclase exotoxins are found in three pathogens which pose significant human health threats. *B. pertussis* infections have seen a recent rise due to relaxed immunization. *P. aeruginosa* is a predominant mortality risk for hospitalized patients. *B. anthracis* presents an infectious challenge to third-world countries and has been developed as a biological weapon. The structure of EF-CaM indicates that the catalytic sites of these three bacterial enzymes are highly conserved but significantly different from the active site of mAC. Thus, the EF-CaM structure will provide a good starting point for future, structure-based inhibitor design efforts aimed at these human pathogens.

Example 8

Purification of H6-EF3, EF3-CH6 and Calmodulin

The adenylyl cyclase domain of EF (291-800) was engineered with a hexahistidine tag on either its N- or C- terminus under the control of a prokaryotic Trc promoter, named H6-EF3 and EF3-CH6, respectively. The purification of EF3-CH6 and H6-EF3 (both pI=8.9) was performed with modifications to that described (Drum et al., 2000). Briefly, crude *Escherichia coli* (*E. coli*) lysate was flowed over a DEAE column to remove acidic *E. coli* proteins and directly onto a Macro-S column. A salt gradient was then applied only to the Macro-S column and the peak fraction containing EF3 pooled. The enriched EF3 was loaded onto a nickel-chelating sepharose column and eluted with 100 mM imidazole (pH 7.0). The greater than 95% pure EF3 protein was then further purified with a Pharmacia Source-S column. The purity of the resultant Edema Factor was greater than 98% and was concentrated to greater than 40 mg/ml. The protein could be stored at −8° C. in 10 mM Tris pH 7.5 buffer. Typical yields for a prep of H6-EF3 and EF3-CH6 gave 80 mg and 45 mg from a 12-liter *E. coli* culture, respectively. Purification of calmodulin was carried out through induction of the expression plasmid pAED4-hCaM in *E. coli* BL21(DE3) cells as described (Drum et al., 2000).

Example 9

Crystallization of EF Without Substrate and EF-CaM Without Substrate

In one embodiment, EF-3 proteins with either hexahistidine-tagged N-terminal or C-terminal ends (H6-EF3 or EF3-CH6, respectively) were purified as described. Crystals of EF alone were grown by the hanging drop method. 1 μL of 40 mg/mL H6EF-3 in 20 mM Tris, pH 7.5, 50 mM NaCl, was mixed with 1 μL of a well solution containing 100 mM citric Acid, (pH 5.65, adjusted with NaOH), 15% glycerol, PEG 550 MME at 11.5% w/v, 220 mM $NiSO_4$, and 2 mM $MgCl_2$. Within one to three weeks, crystals with the $P2_12_12$ space group were formed as a bundle. The EF alone crystal clusters were surgically separated into the single crystals. The crystals were then equilibrated for 5 minutes in cryoprotectant containing the well buffer with the glycerol percentage adjusted to 30% w/v. Crystals of nucleotide-free EF3-CH6/CaM complex in the 1222 spacegroup were grown and cryoprotected as described with the exception that no ATP analog was added during cryoprotection. Crystals were frozen in liquid propane and mounted in a 100° K nitrogen stream. Data were collected at APS Biocars 14-BM-C (EF alone) and NSLS X25 (EF-CaM complex), and processed with HKL OR Mosflm.

In another embodiment, all crystals of EF3-calmodulin complex were grown by the hanging drop method. The protein solution (2 ml) was mixed in a 1:1 ratio with the crystallization buffer and allowed to equilibrate via vapor diffusion over 500 ml of well solution at 4° C. Crystal-Screen One and Two (Hampton Research) were used to find crystallization conditions for Edema Factor in complex with calmodulin. Initially, a large proportion of the screened conditions produced a large precipitate upon mixing with the protein. In each case where this occurred, the condition was diluted in the well until precipitation was no longer observed in a newly setup drop. Refinement of the initial condition resulted in single crystals that would grow in approximately 3-6 weeks (Table 3). Lanthanide and 3'-deoxy ATP (5 mM), a non-hydrolyzable ATP analog both facilitated crystal seeding and growth. The washed crystals were analyzed by SDS-PAGE and mass spectrometry and appeared to contain EF3 and calmodulin in 1:1 ratio. Although both H6-EF3 and EF3-CH6 could form crystals when mixed with calmodulin, the best diffraction and most regular crystallization kinetic were observed with EF3-CH6, the C-terminal, hexahistidine-tagged protein in combination with calmodulin. For heavy metal derivatization, the crystals were soaked with saturated uranium fluoride for 30 min or 10 mM tri-ethyl lead acetate for 2 hours. The approximately 0.4×0.4×0.6 mm-size crystals were transferred into an identical mother-liquor containing 30% glycerol by slowly ramping from the initial glycerol concentration to 30% glycerol over a period of 10 hours and allowing the crystal to soak in the 30% glycerol solution for greater than 12 hours. The crystal was then frozen in liquid propane and data collected at 100K (Table 4). Although many surface fissures were observed on the crystal, x-ray analysis showed relatively low mosaicity and increased diffraction strength compared with similar crystals that were cryo-protected with faster exchange times.

TABLE 3

Crystallization conditions for the crystal forms of EF/calmodulin complex

| | I222 | $P3_121$ | $P2_12_12_1$ |
|---|---|---|---|
| 14.6 mg/ml EF3 | EF3-CH6 | EF3-CH6 | H6-EF3 |
| Calmodulin (mg/ml) | 6.2 | 6.2 | 5.4 |
| 100 mM NaCacodylate | pH 6.5 | pH 6.0 | pH 6.5 |
| Ammonium sulfate (mM) | 350 | 450 | 300 |
| PEG 8,000 (%) | 10 | 10 | 10 |
| Glycerol (%) | 20 | 18 | 0 |
| $MgCl_2$ (mM) | 1 | 2 | 1 |
| $YbCl_3$ (mM) | 0.3 | 0.3 | 0 |

TABLE 4

Statistics of the native and derivatized EF/calmodulin complex data sets. Values in parentheses are the highest resolution shell. No cutoffs were applied to the data for this analysis

| Protein | Native EF3-CH6/calmodulin | EF3-CH6/Se-Met calmodulin | H6-EF3/calmodulin (Uranyl fluoride) | H6-EF3/calmodulin (Tri-ethyl lead acetate) |
|---|---|---|---|---|
| Beamline | APS, 14-BM-C | APS, ID-19 | NSLS, X4a | Rotating anode |
| Space group | I222 | I222 | I222 | I222 |
| a | 117.60 | 116.03 | 116.73 | 116.49 |
| b | 167.44 | 166.33 | 165.39 | 166.88 |
| c | 343.48 | 343.11 | 345.16 | 343.99 |
| Total observations | 875,650a | 261,943 | 100,399 | 118,672 |
| Unique Observations | 80,665 | 29,991 | 24,117 | 33,477 |
| Resolution (Å) | 2.75 | 3.8 | 4.0 | 4.0 |
| Rsym (%) | 9.7 (26.4) | 7.6 (16.4) | 11.0 (34.1) | 11.0 (38.0) |
| I/s(I) | 4.6 (2.8) | 14.0 (8.7) | 4.3 (2.0) | 11.3 (3.5) |
| Completeness(%) | 91.6 (57.2) | 90.1 (92.1) | 80.0 (79.6) | 96.6 (97.7) |
| Multiplicity | 10.9 (3.3) | 8.7 (6.1) | 4.16 (4.2) | 3.54 (3.3) |
| Rmerge (%)[b.] | | 29.0 | 43.7 | 28.9 |
| Phasing Power (acentrics)[c.]: Isomorphous, Anomalous | | peak: 2.18, 1.39; inflection: 2.8, 1.26 | 0.81, 0.82 | 1.17, 0.00 |
| Cullis R (acentrics)[c.]: Isomophorphous, Anomalous | | peak: 0.49, 0.85; inflection: 0.43, 0.88 | 0.96, 0.85 | 0.90, 0.00 | a For the native data set, 120o of data was collected in 0.5o oscillations with two kappa angles separated by 40o. Data was then collected with short exposures to compensate for the multiple overloads observed in the low-resolution reflections.
[b.]Rmerge statistics were generated using SCALEIT (Smith et al., 1992).
[c.]Calculated using SHARP (La Fortelle et al., 1997).

Example 10

Cryoprotection of EF3-CaM Complex

The approximately 0.4×0.4×0.6 mm-size crystals were transferred into an identical mother-liquor containing 30% glycerol by slowly ramping from the initial glycerol concentration to 30% glycerol over a period of 10 hours and allowing the crystal to soak in the 30% glycerol solution for greater than 12 hours. The crystal was then frozen in liquid propane and data collected at 100K (Table 3). Although many surface fissures were observed on the crystal, X-ray analysis showed relatively low mosaicity and increased diffraction strength compared with similar crystals that were cryo-protected with faster exchange times.

Example 11

Data Collection and Processing for EF3-Calmodulin Complex

For the data of EF3-CH6/selono-methionyl calmodulin, an EXAFS study was used to find the selenium K edge before data were collected at inflection point, peak, and remote wavelengths. Initially, the selenium edge was obscured by background fluorescence from the arsenic moiety of 100 mM cacodylic acid, included as the cryoprotectant buffer. However, narrowing of the band pass of the fluorimeter to selectively amplify the selenium fluorescence allowed accurate tuning of the monochromater to the selenium edge. The native data was reduced with MOSFLM (Leslie, 1992), data from the uranium fluoride soak with HKL (Otwinowski et al., 1997), data with seleno-methionyl calmodulin with HKL 2000 (Otwinowski et al., 1997), and data from the tri-ethyl lead acetate soak with XDS (Kabsch, 1993).

Example 12

Results and Discussion of EF3-Calmodulin Complex

Figure 8:
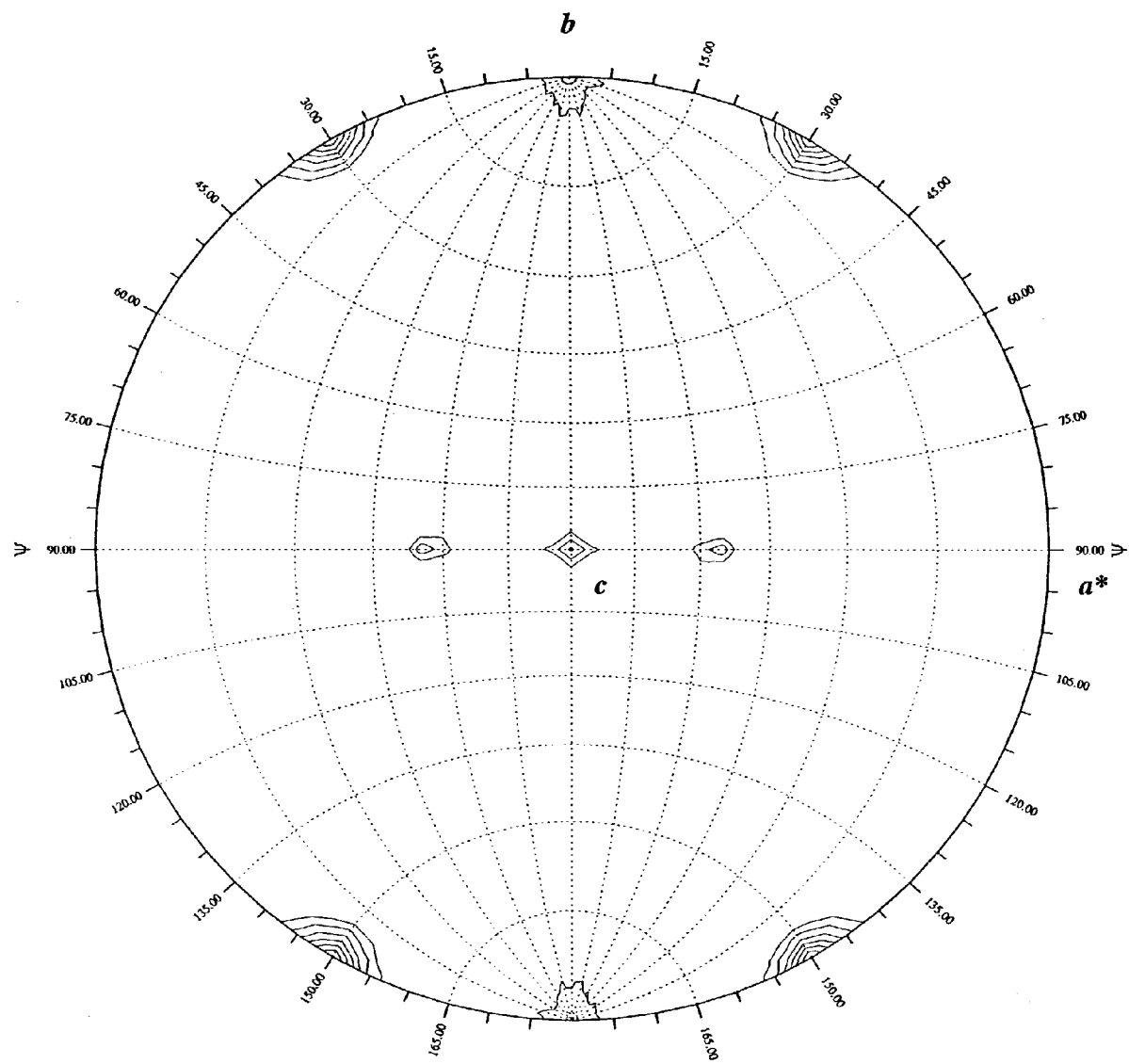
FIG. 8 Self-rotation function with the 1222 crystal form of EF3/calmodulin using native data between 15.0-4.0 Å and a 30.0 Å radius of integration at k=120° section. The plot was contoured starting at 15 s with an interval of 3 s. This figure was calculated using GLRF (Tong, 1990).

Minor changes in crystallization conditions produced crystals of three distinct space groups, I222, P3121, and P212121 (Table 3). Crystals of space group I222 (Table 4) were used for the structure determination because they were the most reproducible and were less often twinned than the other space groups. The EF/calmodulin crystals with p3121 space group have unit cell dimensions of a=b=172.3 ↑, c=196.8 Å and that of P212121 has a unit cell dimension as a=183.5 Å, b=217.3 Å, c=322.9 Å. The assumption of three Edema Factor/calmodulin complexes (228 kDa) in I222 and P3121 asymmetric units, yields a $V_M$ of 3.6 and 4.0 Å3, respectively (solvent content of ~65% and 70%). A similar $V_M$ and solvent content (3.3 Å3 and 62%) predicts twelve EF3/calmodulin complexes in P212121 space group. The presence of several distinct space groups produced by similar crystal conditions suggested a relationship between crystallographic operators and predicted a three-fold non-crystallographic symmetry operator parallel to the b-c diagonal of the I222 space group. A self-rotation function search in the I222 space group reveals a significant peak in the k=120° section at the expected position, confirming the presence of a non-crystallographic three-fold axis in the asymmetric unit (FIG. 8).

The inventors grew crystals from the complex of EF3 and seleno-methionyl calmodulin (Table 4). Calmodulin contains 9 methionines while EF3 has only 3. Selenium incorporation was confirmed by the existance of a peak in the self-rotation function calculated using anomalous difference Patterson maps. This peak was in roughly the same position as that seen in the self rotation function using only native data. After numerous unsuccessful attempts to interpret the anomalous and isomorphous difference Pattersons using HASSP, RSPS (Knight, 2000) and SOLVE (Terwilliger et al., 1999), a direct methods algorithm, Shake-n-Bake (Weeks et al., 1999), was applied to the anomalous differences. Truncating the data at 4 Å and applying an E/σE cutoff of 1, allowed the successful location of 8 of the expected 27 seleniums, resulting in a ratio of 1 resolvable selenium per 167 amino acids. Additional, potential sites located using difference Fourier maps were filtered based on the relative positions of the methionines within a previously solved calmodulin structure (Babu et al., 1985) and the expected three-fold symmetry within the asymmetric unit. After 12 selenium sites had been identified, the solvent flattened phases produced significant peaks in cross Fourier maps from data of crystals soaked with either uranium fluoride or tri-ethyl lead acetate (Table 4), corresponding to 5 U and 5 Pb sites. Using SHARP (La Fortelle et al., 1997), an experimental, 4 Å map was calculated and solvent flattened with DM (Cowtan, 1994).

Due to the poor quality of the initial experimental phases, map averaging was required to identify the remaining 22 heavy atom sites. After skeletonization of the density in MAPMAN (Kleywegt et al., 1999), a mask was drawn around each monomer using MAMA (Kleywegt et al., 1999) and operators relating the three enzymes were refined with IMP (Kleywegt et al., 1997). Maps were rotated and averaged using MAPROT (Stein et al., 1994) and SIGMAA (Read, 1986) was used to combine the back-transformed phases with the original, experimental phases. The improved phases were used to find the remaining 15 Se, 4 U and 3 Pb sites in cross difference Fourier maps, resulting in an overall Figure of merit (FOM) of 0.63 for acentric reflections. A section from FOM- weighted Fo map without density modification is shown in FIG. 8. The resultant, refined operators were used as starting points for eventual iterative averaging, solvent flattening and phase combination and extension from 4 Å to 2.75 Å using DM (Cowtan, 1994).

Figure 9:
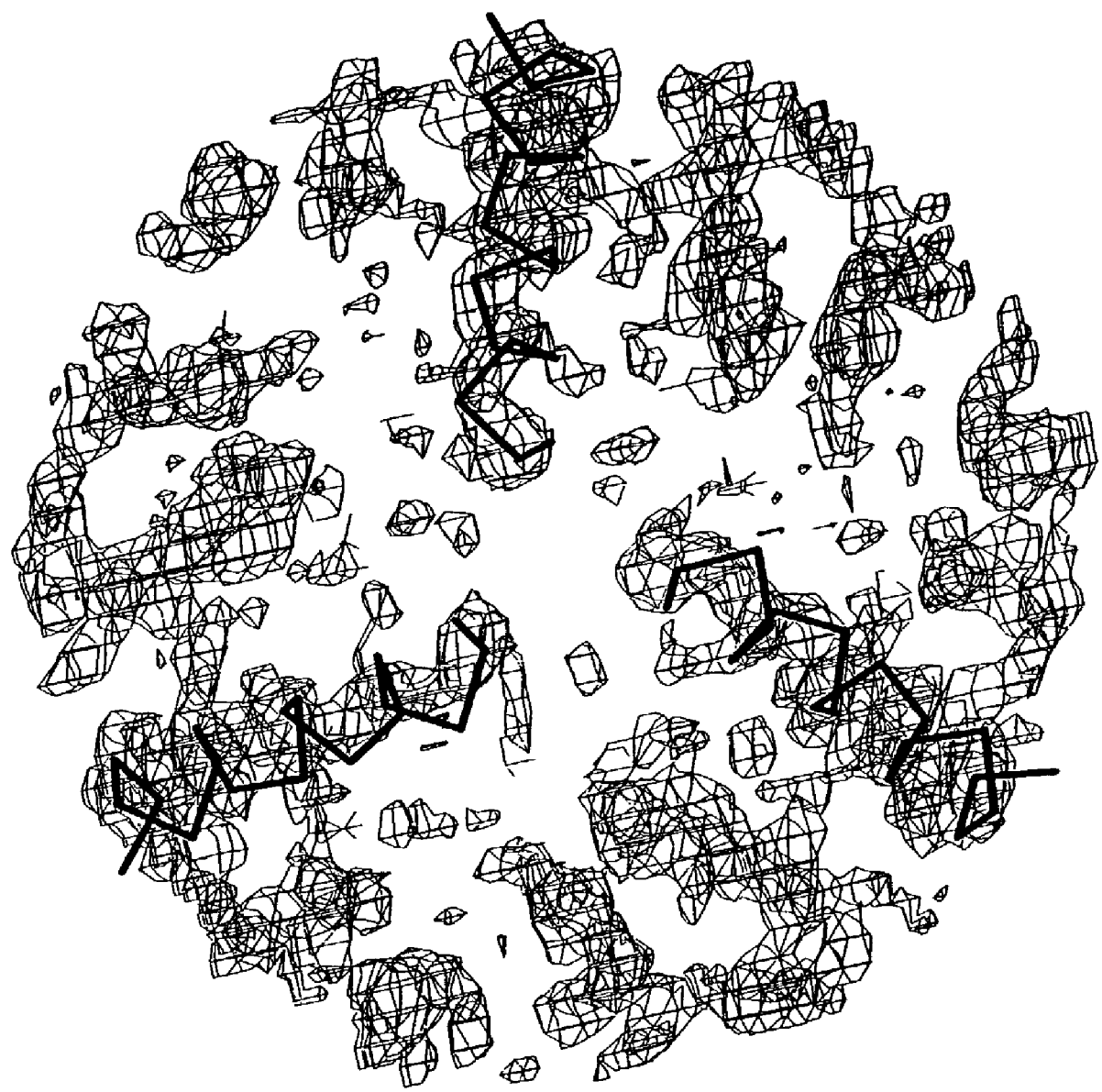
FIG. 9 FOM weighted Fo map calculated from solution of the combined phases from selenomethionine, uranium, and lead. The helices from each of the three non-crystallographically related molecules in the asymmetric unit are shown. This figure was calculated using Xtalview (McRee, 1992).

Although objective evaluation of experimental phases can be difficult, several factors point to the validity of experimental phasing. Unaveraged phases determined from the refinement of all 47 identified heavy atom sites yielded an overall FOM of 0.63 and phasing power and Cullis R statistics for each derivative are listed in Table 2. In the resulting map, electron density with clear secondary structure features is visible and three-fold symmetry is visible within the A.S.U. (FIG. 9), unique from any expected crystallographic symmetry axis and consistent with the solution to the native self-rotation function.

Example 13

Structure Determination and Refinement of EF and EF-Cam

The EF-alone structure was determined by molecular replacement, using the program EPMR and data from 15-4 Å (Table 1). The coordinates for amino acids 294-643 of EF from a preliminary model of EF in complex with CaM and 3'dATP were used to determine initial placement of the single molecule in the asymmetric unit. Holding this solution fixed, amino acids 660-790 were then placed as a rigid body, yielding an overall R-factor of 59% and correlation coefficient on F's of 25%. A single round of rigid body, B-factor and simulated annealing refinement using CNS resulted in working and free R values of 46% and 49%, respectively. The remaining residues were modeled, and the structure was refined using the programs TURBO-FRODO, O, and CNS. The initial solution for the structure of EF-CaM without ATP analog was determined by transferring EF-CaM/3d'ATP coordinates that do not have nucleotide or the nucleotide contacting residues onto the EF-CaM data set. The initial working and free R values were 37% and 44% after simulated annealing refinement in CNS. Additional model building was performed using the program O and iterative cycles of B-factor and simulated annealing using a non-crystallographic three-fold restraint were performed using CNS (Brunger et al., 1998). Calculation for the surface areas was done by using GRASP (Nicholls et al., 1991). Figures were made using Molscript, Povray, GRASP, and David Jeruzalmi's r3dtopov and loosengrasp (Esnouf, 1999; Nicholls et al., 1991).

In another embodiment, two crystal forms of the EF/CaM complex with space group I222 and P3$_1$21 were grown and used in solving the structure (Drum et al., 2001). Both crystal forms contain three complexes in the asymmetric unit, and are related to one another such that the crystallographic symmetry in one space group is closely related to the non-crystallographic symmetry in the other. The best crystals, those of space group I222, diffract to 2.75 Å resolution. The structure was initially solved by multi-wavelength anomalous diffraction (MAD) at 3.8 Å resolution using the signal from the 27 CaM selenomethionines and three Yb$^{2+}$ ions in the asymmetric unit. The initial phase set was improved by inclusion of 4.0 Å uranyl fluoride and triethyl lead acetate derivative data. The 3.8 Å experimental phases were extended to 2.75 Å resolution using iterative cycles of three-fold non-crystallographic symmetry averaging and phase combination in DM[58]. The initial phases for the EF-alone and EF-CaM structures were obtained by molecular replacement using the program EPMR. The residues were modeled, and the structure was refined using the programs TURBO-FRODO, O, and CNS. Calculation for the surface areas was done by using GRASP. The structure was traced using Turbo and O (Jones et al., 1991). Iterative cycles of B-factor and simulated annealing using a non-crystallographic three-fold restraint were performed using CNS (Brunger et al., 1998). Calculation for the surface areas was done by using GRASP (Nicholls et al., 1991). Figures were made using Molscript, Povray, GRASP, and David Jeruzalmi's r3dtopov and loosengrasp (Nicholls et al., 1991; Kraulis, 1991). The search for the structure homolog of EF $C_A$ and $C_B$ domains was performed using NCBI VAST search engine (Gibrat et al., 1996) and the top thirty returns were examined manually.

Example 14

Construction and Analysis of EF Mutants

To construct the plasmids for the expression of mutant proteins, pProExH6-EF3 was used as the template, and the desired mutation was introduced using the Stratagene Quik-Change kit. The resulting mutation was confirmed by DNA sequencing using Perkin Elmer Big-Dye kit. Plasmids for each mutation were then transformed into the RNAseE deficient *E. coli* BL21 Star™ (DE3) containing pUBS520 and mutant proteins were purified to greater than 90% pure as described (Drum et al., 2000). In vitro adenylyl cyclase assays of the purified were performed using a-$^{32}$P-ATP as described (Drum et al., 2000). To ensure that the observed changes in adenylyl cyclase activity of the purified mutant proteins is not due to the clonal variation, two independent plasmid clones for each mutation were then transformed into *E. coli* BL21 Star™ (DE3) containing pUBS520 and the high speed supernatants of *E. coli* lysate prepared. In vitro adenylyl cyclase activity of the EF mutant proteins was performed. In all cases, two independent mutant proteins behave similarly.

Example 15

A Structural Homologue of EF/CaM

Figure 10:
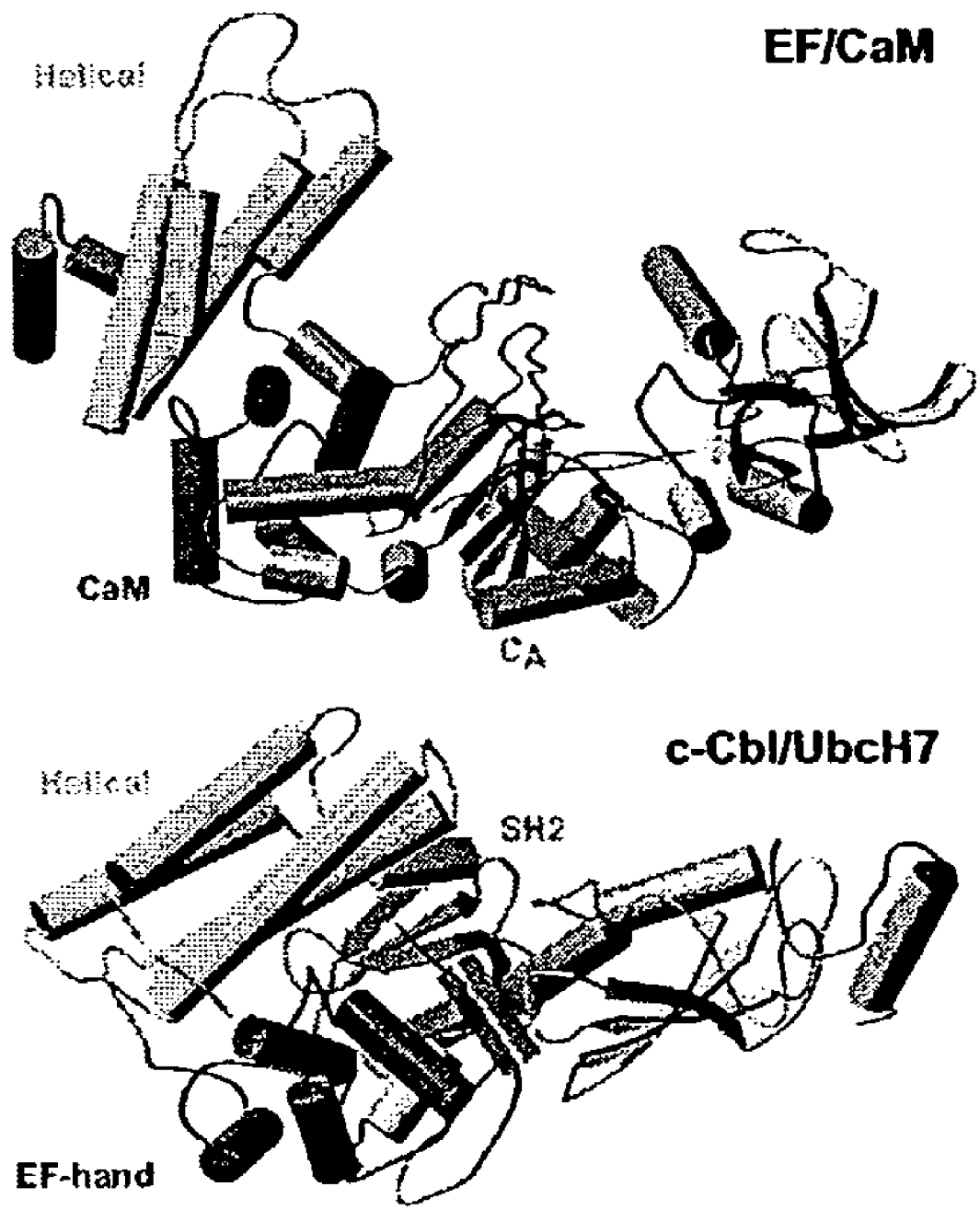
FIG. 10 Depiction of homologous secondary structure elements between the EF/CaM and c-Cb1/UbcH7 complexes. Regions of structure homology are colored by blue (segments of EF $C_B$ and UbcH7), green (segments of EF $C_A$ and c-Cb1-SH2), red (CaM c-terminal and c-Cb1 "EF-hand" domain), and yellow (helical domains of EF and c-Cb1). The RING domain (residues 327-382) of c-Cb1 and the CaM N-terminal domain (residues 82-147) are removed for clarity.

Whereas EF is not homologous to the catalytic core of mAC, each of the four domains of EF/CaM has a structural counterpart within a previously solved complex: that of the tyrosine kinase regulator, Cb1, bound to a ubiquitin conjugating enzyme, Ubc-H7 (FIG. 10) (Meng et al., 1999). EF domain $C_B$ shares structural homology with UbcH7 (2.9 rmsd over 49 aa residues), the $C_A$ domain with the SH2 domain of Cb1 (3.0 rmsd over 50 aa residues), the C-terminus of CaM with the Cb1 calcium binding domain (2.6 rmsd over 61 aa residues), and the helical domain of EF with the helical domain of Cb1 (2.3 rmsd over 48 aa residues). While the interaction of the C-terminal domain of CaM with the helical domain and the $C_B$ domain of EF is reminiscent of Cb1, the contact between UbcH7 and the SH2 domain of Cb1 is significantly different from that of the CA and $C_B$ domains of EF. These two complexes may share a common, ancestor protein in which homologs of these domains are part of a single polypeptide chain. Alternatively, the connection among these four domains may represent a motif for the interaction of these four domains. Also, the homology between $C_A$ and the SH2 domain raises the possibility that EF or its ancestors may interact with tyrosine-phosphorylated eukaryotic proteins.

Example 16

Purification of CyaA and Fluorescence Resonance Energy Transfer of Labeled CaM The expression and purification of recombinant EF and calmodulin protein were performed as described previously (Drum et al, 2000). To express the adenylyl cyclase domain (amino acids 1-412) of CyaA, pET-CyaA1-412 (kindly provided by Dr. Emanuel Hanski at Hebrew Univ.-Hadassah Medical School) (Bejerano et al., 1999) were transformed into *E. coli* B834(DE3) cells harboring pREP4. The resulting cells were cultured at the optimized condition for CyaA expression (19-hour induction at 24° C. with 30 mM IPTG) and the high-speed supernatant of *E. coli* lysate was prepared without denaturant. Recombinant CyaA1-412 with greater than 95% purity was obtained by fractionation through a Ni-chelating column followed by a Q-sepharose column, concentrated to greater than 10 mg/ml, and stored at –80° C. The identity of CyaA1-412 was confirmed by its molecular weight (46,216 daltons based on mass spectrometry, 32 daltons higher than its ideal mass) and its calmodulin-activated adenylyl cyclase activity. The yield is around 12 mg from each liter of *E. coli* culture. To perform the FRET study, CaM34/110, a human CaM mutant in which T34 and T110 were both changed to cysteine was randomly labeled with a fluorescence donor, N-iodoacetyl-N'-(5-sulfo-1-naphtyl)ethylenediamine (1,5-IAEDANS) and a non-fluorescence acceptor, 4-dimethylaminophenylazophenyl-4'-maleimide (DAB) and purified by HPLC. The steady-state fluorescence emission of CaM34/110-AEDANS/DAB was recorded as described (Drum et al., 2000). The dissociation constant between CaM and CyaA and between CaM and the EF helix H peptide was determined by titration of donor-acceptor labeled CaM34/110 with CyaA1-412 protein and EF H peptide, respectively (Drum et al., 2000).

Example 17

Expression of the Catalytic Domain of Edema Factor and CaM

The inventors have developed a novel purification scheme to facilitate large-scale production of Edema Factor. The approach begins with modifications of the Edema Factor gene that replaced the binding region of protective antigen with a hexahistidine tag. Activity of this truncated molecule was probed using an adenylyl cyclase assay. As expected from previous studies (Masure et al., 1991; Masure et al., 1988), the truncated protein had wild-type cyclase activity, which was stimulated upon complex formation with $Ca^{2+}$/CaM. The gene encoding Edema Factor was ligated into a modified pProEx-1 expression vector (Gibco/BRL) to construct expression plasmids coding for the protein with either N- or C-terminal hexahistidine tags. Progressive deletion of residues from the N- and C-termini was performed to search for the optimal construct for the expression of the functional, CaM-sensitive adenylyl cyclase. Deletion of about 300 amino acids from the N-terminus significantly improved the expression of Edema Factor, and its expression could be clearly visualized after the whole-cell lysate was run on a gel under the optimum induction conditions (100 uM IPTG over 12 hours in enriched media at 25 deg.). The induced lysate was first loaded onto DEAE column at pH 7.5. Due to the relative basic pI (8.9) of the Edema Factor, most of the desired protein flowed through the column, which was then loaded onto an S-sepharose (Pharmacia) column. Functional Edema Factor was eluted with a NaCl gradient, loaded onto a nickel-NTA column and eluted with 150 mM imidazole. Eluate from this procedure contained greater than 97% pure Edema Factor, with a small amount of proteolytic contamination as judged by SDS-PAGE and mass spectroscopy. Total yield was approximately 42 mg/L culture, about 10 fold better than that reported previously (Labruyure et al., 1990). Anticipating crystal packing problems that may arise from disordered histidine residues, a C-terminally tagged protein was also constructed and purified via the same strategy. Its yield was lower, 12 mg/L culture, though the proteolytic contamination was mildly reduced.

Full length human and fruit fly CaM's were expressed in bacteria and purified using a previously published protocol (Huber et al., 1996). The major step in the purification of CaM is a hydrophobic interaction column, phenyl sepharose, which has high affinity for CaM in the presence of calcium ion and drastically reduced affinity in the absence of calcium ion. *E. coli* were disrupted by sonication, and the centrifuged lysate was loaded on a phenyl sepharose column in the present of calcium. The column was then washed and CaM was eluted with EDTA or EGTA. The eluate was greater than 95% pure. For x-ray crystallography, the eluate is further purified using an ion exchange column (DEAE or Q-sepharose). This procedure yields ~5-10 mg purified protein per liter of culture.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345

U.S. Pat. No. 4,275,149
U.S. Pat. No. 4,277,437
U.S. Pat. No. 4,282,287
U.S. Pat. No. 4,366,241
U.S. Pat. No. 4,542,102
U.S. Pat. No. 5,252,743
U.S. Pat. No. 5,412,087
U.S. Pat. No. 5,445,934

Affinity Techniques, Enzyme Purification: Part B, Meth. Enz. 34 Jakoby and Wilchek (Eds.), Acad. Press, N.Y. (1974).

Babu et al., "Three-dimensional structure of calmodulin," Nature, 315:37-40, 1985.

Baillie and Read, *Bacillus anthracis*, a bug with attitude," Curr. Opin. Microbiol., 4:78-81, 2001.

Bejerano, Nisan, Ludwig, Goebel, Hanski, "Characterization of the C-terminal domian essential for toxic activity of adenylate cyclase toxin," Mol. Microbiol., 31:381-382, 1999.

Bennett et al., J. Molec. Recog., 8:52-58, 1995.

Bieger and Essen, "Structural analysis of adenylate cyclases from *Trypanosoma brucei* in their nomomeric state," EMBO J., 20:443-445, 2001.

Brunger, Adams, Clore, DeLano, Gros, Grosse-Kunstleve, Jiang, Kuszewski, Nilges, Pannu et al., "Crystallography and NMR system: A new software suite for macromolecular structure determination," Acta Crystallogr D. Biol. Crystallogr, 54:905-921, 1998.

Chattopadhyaya, Meador, Means, Quiocho, "Calmodulin structure refined at 1.7 A resolution," J. Mol. Biol. 228:1177-1192, 1992.

Coligan et al., Current Protocols in Immunology, 1(2): Chapter 5, 1991.

Conte, Chothia, Janin, "The atomic structure of protein-protein recognition sites," J. Mol. Biol., 285:2177-2198, 1999.

Cowtan, Joint CCP4 and ESF-EAMCB Newsletter on Protein Crystallography, 31:34-38, 1994.

Deisseroth, Heist, Tsien, "Translocation of calmodulin to the nucleus supports CREB phosphorylation in hippocampal neurons," Nature, 392:198-202, 1998.

DiAntonio, "Translating activity into plasticity," Nature, 405:1011-1012, 2000.

Dixon, Meselson, Guillemin, Hanna, "Antrhax", N. Engl. J. Med., 341:815-8256, 1999

Doman et al., "Molecular docking and high-throughput screening for novel inhibitors of protein tyrosine phosphatase-1B," J. Medicinal Chem., 45:2213-2221, 2002.

Drum et al., "An extended conformation of calmodulin induces interactions between the structural domains of adenylyl cyclase from *Bacillus anthracis* to promote catalysis," J. Biol. Chem., 275:36334-36340, 2000.

Drum, Shen, Rice, Bohm, Tang, "Crystallization and preliminary X-ray study of the edema factor exotoxin adenylyl cyclase domain from *Bacillus Anthracis* in the presence of its activator, calmodulin," Acta Crystallogr. D. Biol. Crystallogr, 2001.

Duesbery et al., "Proteolytic inactivation of MAP-kinase-kinase by anthrax lethal factor," Science, 280:734-737, 1998.

Ehlers and Augustine, "Calmodulin at the channel gate," Nature, 399:105, 1999.

Eldik and Watterson, "Calmodulin and signal transduction," (NEED JOURNAL), 1998.

Esnouf, "Further additions to MolScript version 1.4, including reading and contouring of electron-density maps, Acta Crystallogr D. Biol. Crystallogr, 55:938-940, 1999.

Farrar, Lukas, Craig, Watterson, Carlson, "Features of calmodulin that are important in the activation of the catalytic subunit of phosphorylase kinase," J. Biol. Chem., 268:4120-4125, 1993.

Finn et al, "Calcium-induced structural changes and domain autonomy in calmodulin," Nat. Struct. Biol., 2:777-783, 1995.

Galburt et al., "A novel endonuclease mechanism directly visualized for I-Ppol," Nat. Struct. Biol., 6:1096-1099, 1999.

Gibrat, Madej, Bryant, "Surprising similarities in structure comparison," Curr. Opin. Struct. Biol., 6:377-385, 1996.

Glaser et al., "Functional consequences of single amino acid substitutions in calmodulin-activated adenylate cyclase of *Bordetella pertussis*, EMBO J., 10:1683-1688, 1991.

Hanna, Anthrax pathogenesis and host response," *Curr. Topics in Microbio. And Immunol.,* 225:13-35, 1998

Hayashi, Izumi, Titani, Matsushima, "The binding of myristolylated N-terminal nonapeptie from neuro-specific protein CAP-23/NAP-22 to calmodulin does not induce the globular structure observed for the calmodulin-nonmyristylated peptide complex," *Protein Sci.,* 9:1905-1913, 2000.

Huang et al., "Structure of a WW domain containing fragment of dystrophin in complex with beta-dystroglycan," *Nat. Struct. Biol.,* 7:634-638, 2000.

Huber, El-Mezgueldi, Grabarek, Slatter, Levine, Marston, "Multiple-sited interaction of caldesmon with $Ca^{(2+)}$-calmodulin," *Biochem. J.,* 316:413-420, 1996.

Immobilized Biochemicals and Affinity Chromatography, Adv. Exp. Med. Biol. 42 (ed. R. Dunlap, Plenum Press, N.F. 1974

Inglesby et al., "Anthrax as a biological weapon: updated recommendations for management," *JAMA,* 298:2236-2252, 2002.

Johanson et al., *J. Biolog. Chem.,* 270(16):9459-9471, 1995.

Kabsch, *J. Appl. Cryst.,* 26:795-800, 1993.

Kleywegt and Jones, *Acta Crystallogr D. Biol. Crystallogr,* 55:941-944, 1999.

Kleywegt and Read, *Structure,* 5:1557-1569, 1997.

Knight, *Acta Crystallogr D. Biol. Crystallogr.,* 56:42-47, 2000.

Kraulis, "Molscript: a program to produce both detailed and schematic plots of protein structures," *Appl. Crystallogr,* 24:946-950, 1991.

Krueger, Gallagher, Wang, Trewhella, "Calmodulin remains extended upon binding to smooth muscle caldesmon: a combined small-angle scattering and fourier transform infrared spectroscopy study," *Biochemistry,* 39:3979-3987, 2000.

Krueger, Gallahger, Zhi, Geguchadze, Persechini, Stull, Trewhella, "Activation of myosin light chain kinase requires translocation of bound calmodulin," *J. Biol. Chem.,* 276: 4535-4538, 2001.

Kuboniwa et al., "Solution structure of calcium-free calmodulin," *Nat. Struct. Biol.,* 2:768-776, 1995.

Labruyure et al., "Characterization of ATP and calmodulin-binding properties of a truncated form of *Bacillus anthracis* adenylate cyclase," *Biochemistry,* 29:4922-4928, 1990.

Ladant and Ullmann, "*Bordatella pertussis* adenylate cyclase: a toxin with multiple talents," *Trends Microbiol.,* 7:172-176, 1999.

LaFortelle and Bricogne, *Methods in Enzymology,* 276: 472-494, 1997.

Leppla, "Anthrax toxin edema factor: a bacterial adenylate cyclase that increases cyclic AMP concentrations of eukaryotic cells," *Proc. Natl. Acad. Sci. USA,* 79:3162-3166, 1982.

Leppla, "Anthrax toxins," In: *Bacterial toxins and virulenece factors in disease*, Moss et al., (Eds.), NY, Base, Hong Kong Mercel Kekker, 543-572, 1998.

Leppla, "*Bacillus anthracis* calmodulin-dependent adenylate cyclase: chemical and enzymatic properties and interactions with eucaryotic cells," *Adv. Cyclic Nucleotide Protein Phosphorylation Res.*, 17:189-198, 1984.

Leslie, In: *Joint CCP4 and ESF-EAMCB Newsletter on Protein Crystallography*, (26) 1992

Lewit-Bentley and Rety, "EF-hand calcium-binding proteins," *Curr. Opin. Struct. Biol.*, 10:637,643, 2000.

Lorber et al., "Protein-protein docking with multiple residue conformations and residue substitutions," *Protein Science*, 11:1393-1408, 2002.

Masure, Donovan, Storm, "Purification and assay of cell-invasive form of calmodulin- sensitive adenylyl cyclase from *Bordetella pertussis*, *Methods in Enzymol.*, 195:137-152, 1991.

Masure, Oldenburg, Donovan, Shattuck, Storm, "The interaction of $Ca^{2+}$ with the calmodulin-sensitive adenylate cyclase from *Bordetella pertussis*, *J. Biol. Chem.*, 263:6933-6940, 1988.

McRee, *J. Mol. Graphics*, 10:44-46, 1992.

Meador, Means, Quiocho, "Target enzyme recognition by calmodulin: 2.4 A structure of a calmodulin-peptide complex," Science, 257:1251-1255, 1992.

Meador, Means, Quiocho, "Modulation of calmodulin plasticity in molecular recognition on the basis of x-ray structures," *Science*, 262:1718-1721, 1993.

Meng, Sawasdikosol, Burakoff, Eck, "Structure of the amino-terminal domain of Cb1 complexed to its binding site on ZAP-70 kinase," *Nature*, 398:84-90, 1999.

Michankin et al., "Adenylate-cyclase," *Bulletin de la Societe de Pathologie Exotique*, 85:17-21, 1992.

Miller, Cai, Krause, "The active site of *Serratia* endonuclease contains a conserved magnesium-water cluster," *J. Mol. Biol.*, 288:975-987, 1999.

Mock and Fouet, "Anthrax", *Annul Rev. Microbiol*, 55:647-671, 2001.

Montgomery, Romanov, Guillemette, "Removal of a putative inhibitory element reduces the calcium-dependent calmodulin activation of neuronal nitric-oxide synthase," *J. Biol. Chem.*, 275:5052-5058, 2000.

Munier et al., "Structural characterization by nuclear magnetic resonance spectroscopy of a genetically engineered high-affinity calmodulin-binding peptide derived from *Bordetella pertussis* adenylate cyclase," *Arch. Biochem. Biphys.*, 320:224-235, 1995.

Munier et al., "The role of histidine 63 in the catalytic mechanism of *Bordetella pertussis* adenylate cyclase," *J. Biol. Chem.*, 267:9816-9820, 1992.

Nakamura et al., In: *Handbook of Experimental Immunology* (4th Ed.), Weir, Herzenberg, Blackwell, Herzenberg, (eds). Vol. 1, Chapter 27, Blackwell Scientific Publ., Oxford, 1987.

Nassar, Hoffrnan, Manor, Clardy, Cerione, "Structures of Cdc42 bound to the active and catalytically compromised forms of Cdc42GAP," *Nat. Struct Biol.*, 5:1047,1052, 1998.

Nicholls, Sharp, Honig, "Protein folding and association: insights from the interfacial and thermodynamic properties of hydrocarbons," *Proteins*, 11:281-296, 1991.

Osawa, Tokumitsu, Swindells, Kurihara, Orita, Shibanuma, Furuya, Ikura, "A novel target recognition revealed by calmodulin in complex $Ca^{2+}$-calmodulin-dependent kinase kinase," *Nat. Struct. Biol.*, 6:819-824, 1999.

Otwinowski and Minor, In: *Processing of X-ray Diffraction Data Collected IN Oscillation Mode*, Carter and Sweet (Eds.), *Methods in Enzymology*, Academic Press, (276), 1997.

Parkhill et al., "Genome sequence of *Yersinia pestis*, the causative agent of plague," *Nature* 413:523-527, 2001.

PCT Patent Publication No. 90/07582

PCT Patent Publication No. 91/00868

PCT Patent Publication No. 91/07087

Peters and Mayer, $Ca^{2+}$/calmodulin signals the completion of coking and triggers a late step of vacuole fusion," *Nature*, 396:575-580, 1998.

Pitt, Zuhlke, Hudmon, Schulman, Reuter, Tsien, "Molecular basis of calmodulin tethering and $Ca^{2+}$-dependent inactivation of L-type $Ca^{2+}$ channels," *J. Biol. Chem.*, 276:30794-30802, 2001.

Powers and Shoichet, "Structure-based approach for binding site identification on AmpC beta-lactamase," *J. Medicinal Chem.*, 45:3222-3234, 2002.

Read, *Acta Cryst.*, A42:140-149, 1986.

Remington's Pharmaceutical Sciences, 18th Ed. Mack Printing Company, 1990

Rhoads and Friedberg, "Sequence motifs for calmodulin recognition," *FASEB J.*, 11:331-340, 1997.

Rittinger, Walker, Eccleston, Smerdon, Gamblin, "Structure at 1.65 A of RhoA and its GTPase-activating protein in complex with a transition-state analogue," *Nature*, 389:758-762, 1997.

Sambrook et. al., In: *Molecular Cloning: A Laboratory Manual*, 2d Ed., Cold Spring Harbor Laboratory Press, Cold Spring Harbor, N.Y., 1989.

Scheffzek, Ahmadian, Kabsch, Wiesmuller, Lautwein, Schmitz, Wittinghofer, "The Ras-RasGAP complex: structural basis for GTPase activation and its loss in oncogenic Ras mutants," *Science*, 277:333-338, 1997.

Scherer and Graff, "Calmodulin differentially modulates Smad1 and Smad2 signaling," *J. Biol. Chem.*, 275:41430-41438, 2000.

Schumacher, Rivard, Bachinger, Adelman, "Structure of the gating domain of a $Ca^{2+}$-activated $K^+$ channel complexed with $Ca^{2+}$/calmodulin," *Nature*, 410:1120-1124, 2001.

Shevchenko and Mishankin, "Adenylyl cyclase of the causative agent of plague: its purification and properties," *Zh Mikrobiol. Epidemiol. Immunobiol.*, 7:59-63, 1987.

Shoichet et al., "Lead discovery using molecular docking," *Current Opin. Chem. Biol.*, 6:439-446, 2002.

Shoichet et al., "Ligand solvation in molecular docking," *Proteins*, 34:4-16, 1999.

Stein, Boodhoo, Armstrong, Cockle, Klein, Read, *Structure*, 2:45-57, 1994.

Su et al., "Docking molecules by families to increase the diversity of hits in database screen: computational strategy and experimental evaluation," *Proteins*, 42:279-293, 2001.

Swanljung-Collins and Collins, "$Ca^{2+}$ stimulates the $Mg^{2+}$-ATPase activity of brush border myosin I with three or four calmodulin light chains but inhibits with less than two bound," *J. Biol. Chem.*, 266:1312-1319, 1991.

Tang and Hurley, "Catalytic mechanism and regulation of mammalian adenylyl cyclases," *Mol Pharmacol.*, 54:231-240, 1998.

Tang, Krupinski, Gilman, "Expression and characterization of calmodulin-activated (type1) adenylylcyclase," *J. Biol. Chem.*, 266:8595-8603, 1991.

Terwilliger and Berendzen, *Acta Crystallogr D. Biol. Crystallogr*, 55:849-861, 1999.

Tesmer et al., "Two-metal-Ion catalysis in adenylyl cyclase," *Science*, 285:756-760, 1999.

Tesmer, Berman, Gilman, Sprang, "Structure of RGS4 bound to AIF$_4$-activated G$_{i\alpha 1}$:stabilization of the transition state for GTP hydrolysis," *Cell,* 89:251-261, 1997.

Tesmer, Sunahara, Gilman, Sprang, "Crystal structure of the catalytic domains of adenylyl cyclase in a complex with G$_{s\alpha}$GTPγS," *Science,* 278:1907-1916, 1997.

Tong and Rossman, *Acta Cryst.,* A46:783-792, 1990.

Trewhella, Blumenthal, Rokop, Seeger, "Small-angle scattering studies show distinct conformations of calmodulin in its complexes with two peptides based on the regulatory domain of the catalytic subunit of phosphorylase kinase," *Biochemistry,* 29:9316-9324, 1990.

Wang, Zhuang, Kordowska, Graberek, Wang, "Calmodulin binds to caldesmon in an antiparallel manner," *Biochemistry,* 36:15026-15034, 1997.

Wei et al., "A model binding site for testing scoring functions in molecular docking," *J. Mol. Biol.,* 322:339-355, 2002.

Weeks and Miller, *J. Appl. Cryst.,* 32:120-124, 1999.

Wilson and Brunger, "The 1.0 A crystal structure of Ca$^{2+}$-bound calmodulin: an analysis of disorder and implications for functionally relevant plasticity," *J. Mol Biol.,* 301:1237-1256, 2000.

Yahr Vallis,k Hancock, Barbieri, Frank, "ExoY, an adenylate cyclase secreted by the *Pseudomonas aeruginosa* type III system," *Proc. Natl. Acad. Sci. USA,* 95:13899-13904, 1998.

Yan, Huang, Shaw, Tang, "The conserved asparagine and arginine are essential for catalysis of mammalian adenylyl cyclase," *J. Biol.1 Chem.,* 272:12342-12349, 1997.

Zhang, Tanaka, Ikura, "Calcium-induced conformational transition revealed by the solution structure of apo calmodulin," *Natl. Struct. Biol.,* 2:758-767, 1995.

---

What is claimed is:

1. A method of assaying for an inhibitor of infection by a bacteria comprising:
   selecting a potential inhibitor of a calmodulin activated adenylyl cyclase exotoxin by modeling the inhibitor using structural coordinates of a calmodulin activated adenylyl cyclase exotoxin;
   obtaining the selected potential inhibitor;
   obtaining a calmodulin activated adenylyl cyclase exotoxin;
   obtaining calmodulin;
   admixing the potential inhibitor, the exotoxin, and the calmodulin; and
   assaying to determine whether or not the potential inhibitor inhibits production of cAMP by the exotoxin.

2. The method of claim 1, wherein the bacterial infection is *Bacillus anthracis*, or *Bordetella pertussis*.

3. The method of claim 1, wherein the calmodulin activated adenylyl cyclase exotoxin is Edema Factor from *Bacillus anthracis*.

4. The method of claim 1, wherein the potential inhibitor is a protein, a small molecule, a modified nucleotide, or an antibody.

5. A method of assaying for an inhibitor of infection by a bacteria comprising:
   selecting a potential inhibitor of an adenylyl cyclase exotoxin by modeling the inhibitor using structural coordinates of a calmodulin activated adenylyl cyclase exotoxin;
   obtaining the selected potential inhibitor;
   obtaining an adenylyl cyclase exotoxin;
   admixing the potential inhibitor and the exotoxin; and
   assaying to determine whether or not the potential inhibitor inhibits production of cAMP by the exotoxin.

6. The method of claim 5, wherein the bacterial infection is *Pseudomonas aeruginosa*.

7. The method of claim 5, herein the adenylyl cyclase exotoxin is a homolog of *Bacillus Anthracis* Edema Factor from *Pseudomonas aeruginosa*.

* * * * *

UNITED STATES PATENT AND TRADEMARK OFFICE
CERTIFICATE OF CORRECTION

| | |
|---|---|
| PATENT NO. | : 7,462,472 B2 |
| APPLICATION NO. | : 10/286452 |
| DATED | : December 9, 2008 |
| INVENTOR(S) | : Wei-Jen Tang and Andrew Bohm |

It is certified that error appears in the above-identified patent and that said Letters Patent is hereby corrected as shown below:

In title page, item (73) Assignees, line 3, delete "MD" and insert --MA-- therefor.

In claim 7, column 46, line 54, delete "herein" and insert --wherein-- therefor.

Signed and Sealed this

Twenty-fourth Day of February, 2009

JOHN DOLL
*Acting Director of the United States Patent and Trademark Office*